(12) United States Patent
Yamaji

(10) Patent No.: US 9,782,087 B2
(45) Date of Patent: Oct. 10, 2017

(54) HEART RATE ESTIMATING APPARATUS AND METHOD

(71) Applicant: FUJITSU LIMITED, Kawasaki-shi, Kanagawa (JP)

(72) Inventor: Takayuki Yamaji, Yokohama (JP)

(73) Assignee: FUJITSU LIMITED, Kawasaki (JP)

( * ) Notice: Subject to any disclaimer, the term of this patent is extended or adjusted under 35 U.S.C. 154(b) by 512 days.

(21) Appl. No.: 13/915,689

(22) Filed: Jun. 12, 2013

(65) Prior Publication Data

US 2014/0058254 A1    Feb. 27, 2014

(30) Foreign Application Priority Data

Aug. 22, 2012   (JP) .................................. 2012-183407

(51) Int. Cl.
| | | |
|---|---|---|
| A61B 5/05 | (2006.01) | |
| A61B 5/024 | (2006.01) | |
| A61B 5/00 | (2006.01) | |

(52) U.S. Cl.
CPC .......... *A61B 5/024* (2013.01); *A61B 5/02438* (2013.01); *A61B 5/0507* (2013.01); *A61B 5/7257* (2013.01); *A61B 2562/0204* (2013.01); *A61B 2562/0219* (2013.01)

(58) Field of Classification Search
None
See application file for complete search history.

(56) References Cited

U.S. PATENT DOCUMENTS

| | | | | |
|---|---|---|---|---|
| 4,638,808 A | * | 1/1987 | Mawhinney | .................. 600/430 |
| 8,562,526 B2 | | 10/2013 | Heneghan et al. | |
| 2007/0142715 A1 | * | 6/2007 | Banet et al. | .................. 600/301 |
| 2010/0130873 A1 | * | 5/2010 | Yuen et al. | .................. 600/484 |

FOREIGN PATENT DOCUMENTS

| | | |
|---|---|---|
| EP | 2430975 A1 | 3/2012 |
| JP | 01-115344 | 5/1989 |
| JP | 05-288760 | 11/1993 |
| JP | 2005-237569 | 9/2005 |
| JP | 2008-099849 | 5/2008 |

(Continued)

OTHER PUBLICATIONS

Chawla, M.P.S. et al., "A new statistical PCA-ICA algorithm for location of R-peaks in ECG," International Journal of Cardiology, vol. 129, No. 1, Sep. 16, 2008, pp. 146-148, XP024526205.

(Continued)

*Primary Examiner* — James Kish
(74) *Attorney, Agent, or Firm* — Fujitsu Patent Center

(57) ABSTRACT

A heart rate estimating apparatus may include a transmitter to transmit microwave with respect to a subject, a receiver to receive and detect reflected wave from the subject irradiated with the microwave, and acquire a detected result, a sensor to sense a movement of the subject, and acquire a sensed result, and an estimating unit. The estimating unit may estimate a heart rate based on feature points remaining after excluding, from heart rate candidates, feature points that are obtained by frequency analysis of the detected result and are located in a vicinity of frequencies at which feature points are obtained by frequency analysis of the sensed result.

16 Claims, 24 Drawing Sheets

(56) References Cited

FOREIGN PATENT DOCUMENTS

| JP | 2009-055997 | 3/2009 |
| JP | 2011-050604 | 3/2011 |
| WO | WO-2010/077997 A2 | 7/2010 |

OTHER PUBLICATIONS

Kwon, Sungjun et al., "Validation of heart rate extraction through an iPhone accelerometer," $33^{rd}$ Annual International Conference of the IEEE EMBS, Boston, Massachusetts, Aug. 30, 2011, pp. 5260-5263, XP032111008.

Extended European Search Report dated Nov. 7, 2013 for corresponding European Application No. 13171500.5.

* cited by examiner

HEART RATE ESTIMATING APPARATUS AND METHOD

CROSS-REFERENCE TO RELATED APPLICATIONS

This application is based upon and claims the benefit of priority of the prior Japanese Patent Application No. 2012-183407, filed on Aug. 22, 2012, the entire contents of which are incorporated herein by reference.

FIELD

The embodiments discussed herein are related to a heart rate estimating apparatus, a heart rate estimating method, and a computer-readable storage medium.

BACKGROUND

In this specification, a person (or user) who is a target of heart rate measurement or heart rate estimation, will be referred to as a "subject", for the sake of convenience. Various heart rate measuring apparatuses have been proposed to measure a heart rate by making contact with the subject. However, in the case of the contact type heart rate measuring apparatus, an exclusive sensor, such as an ear clip to be worn on the subject's ear, for example, is used. For this reason, the contact type heart rate measuring apparatus may not be easy to use, and the ear clip may come off from the subject's ear. Hence, it may be difficult to realize a heart rate measuring apparatus capable of positively measuring the heart rate while the subject moves, such as when the subject walks.

On the other hand, a non-contact type heart rate measuring apparatus may detect reflected wave from breast or the like of the subject irradiated with microwave, for example, and estimate the heart rate of the subject by utilizing the Doppler effect. More particularly, because the reflected wave from the subject changes when a distance between a microwave transmitter and the subject changes, the heart rate may be estimated by measuring a displacement of a body surface or an organ, such as the heart, caused by the heart beat. For example, the microwave may have a wavelength of 1 m to 100 pm and a frequency of 300 MHz to 3 THz.

However, the reflected wave from the subject may include reflected wave related to various information other than heart rate information. The reflected wave related to the various information other than the heart rate information may include the reflected wave from other than the body surface of the subject undergoing the displacement caused by the heart beat, such as the body surface of the subject undergoing a displacement caused by breathing, clothing worn by the subject, and the like. When the subject moves by walking, for example, the heart rate and a respiration rate tend to increase, and a shape of the clothing also changes. For this reason, the reflected wave related to the various information other than the heart rate information changes depending on a movement and the like of the subject.

The various information other than the heart rate information may be regarded as noise with respect to the heart rate information, and the accuracy of the heart rate estimation may be difficult to improve when the noise is mixed to the reflected wave. The accuracy of the heart rate estimation may be difficult to improve particularly because it is difficult to eliminate the noise that changes depending on the movement of the subject.

Various techniques are proposed in Japanese Laid-Open Patent Publications No. 2009-55997, No. 2011-50604, No. 2008-99849, No. 2005-237569, No. 5-288760, and No. 1-115344, for example.

In the conventional non-contact type heart rate measuring apparatuses, it may be difficult to improve the accuracy of the heart rate estimation because separation of the heart rate information, by eliminating the noise that changes depending on the movement of the subject, is difficult.

SUMMARY

Accordingly, it is an object in one aspect of the embodiment to provide a heart rate estimating apparatus, a heart rate estimating method, and a computer-readable storage medium, which may improve the accuracy of the heart rate estimation.

According to one aspect of the present invention, a heart rate estimating apparatus may include a transmitter configured to transmit microwave with respect to a subject; a receiver configured to receive and detect reflected wave from the subject irradiated with the microwave, and acquire a detected result; a sensor configured to sense a movement of the subject, and acquire a sensed result; and an estimating unit configured to estimate a heart rate based on feature points remaining after excluding, from heart rate candidates, feature points that are obtained by frequency analysis of the detected result and are located in a vicinity of frequencies at which feature points are obtained by frequency analysis of the sensed result.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS

Preferred embodiments of the present invention will be described with reference to the accompanying drawings.

The disclosed heart rate estimating apparatus, heart rate estimating method, and computer-readable storage medium may receive and detect reflected wave from a subject irradiated with microwave to acquire a detected result, and sense a movement of the subject to acquire a sensed result. A heart rate may be estimated based on feature points remaining after excluding, from heart rate candidates, feature points that are obtained by frequency analysis of the detected result and are located in a vicinity of frequencies at which feature points are obtained by frequency analysis of the sensed result.

A description will now be given of the heart rate estimating apparatus, the heart rate estimating method, and the computer-readable storage medium in each embodiment according to the present invention.

Figure 1:
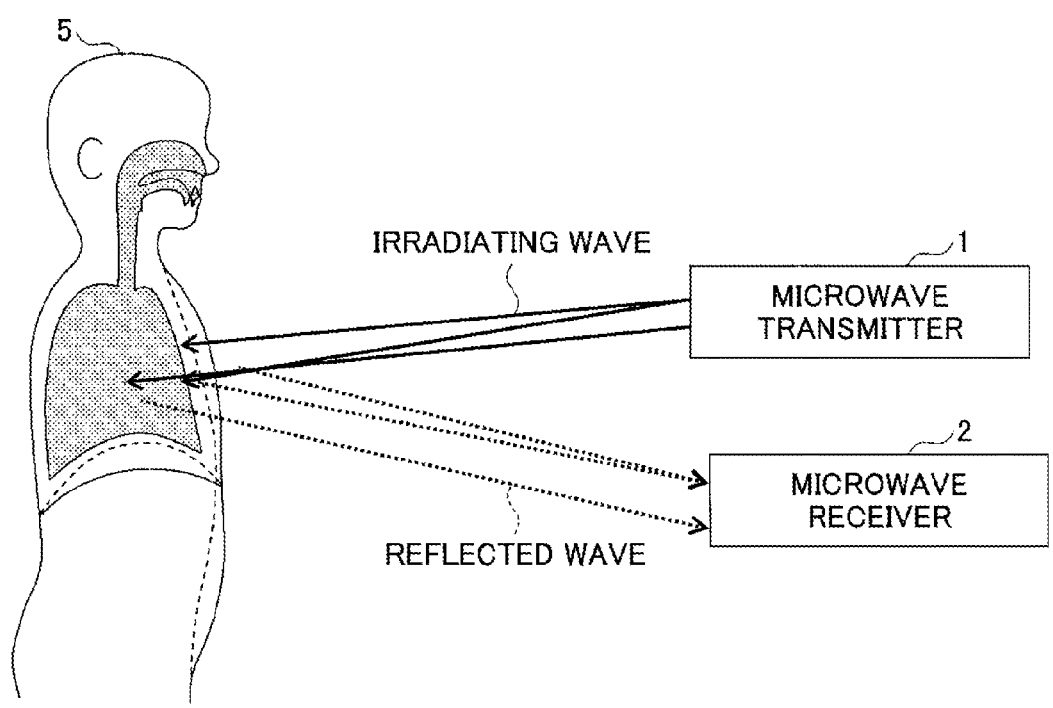
FIG. 1 is a diagram for explaining an example of a non-contact type heart rate estimating apparatus.

FIG. 1 is a diagram for explaining an example of a non-contact type heart rate estimating apparatus. A microwave transmitter 1 may transmit microwave with respect to the breast of a subject 5, for example. A microwave receiver 2 may receive and detect reflected wave from the subject 5 irradiated with the microwave, and acquire a detected result. In the case of an adult subject, an amount of blood that is made to flow in one heart beat may be on the order of 80 ml, and the heart expands and contracts to make the heart beat. Hence, a heart rate may be estimated from an amount of change in the detected result, that is, the change in the reflected wave from the subject 5.

The reflected wave from the subject 5 may include a relatively large amount of noise caused by a change in the distance between the microwave transmitter 1 and the subject 5. For example, clothing worn by the subject 5 may act as a mask that changes its shape depending on a movement of the subject 5, and it may be difficult to identify the reflected wave from the mask that changes its shape in such a manner. For this reason, the reflected wave from a body surface of the subject 5 and the reflected wave from the clothing worn by the subject 5 may be difficult to distinguish, and it may be difficult to accurately detect the distance between the microwave transmitter 1 and the subject and acquire the change in the distance.

The present inventor noted that the change in the distance between the microwave transmitter 1 and the subject 5 is caused by the movement of the subject 5, and conceived a relatively simple process to eliminate the noise caused by the change in the distance between the microwave transmitter 1 and the subject 5, that is, the noise that changes depending on the movement of the subject 5. This process may exclude, from heart rate candidates, peaks (or feature points) that are obtained by frequency analysis of the detected result acquired by the microwave receiver 2 and are located in a vicinity of frequencies at which peaks (or feature points) are obtained by frequency analysis of the sensed result acquired by the sensor. As will be described later, the movement of the subject 5 may be sensed by a sensor, such as a microphone, an acceleration sensor, an angular velocity sensor, and the like, that acquires a sensed result. In addition, because the movement of the body caused by the heart beat is small compared to the movement of the body when the subject 5 walks, for example, it may be convenient in that there is only a low possibility of the sensor configured to detect the movement of the subject 5 detecting the movement of the body caused by the heart beat.

Figure 2:
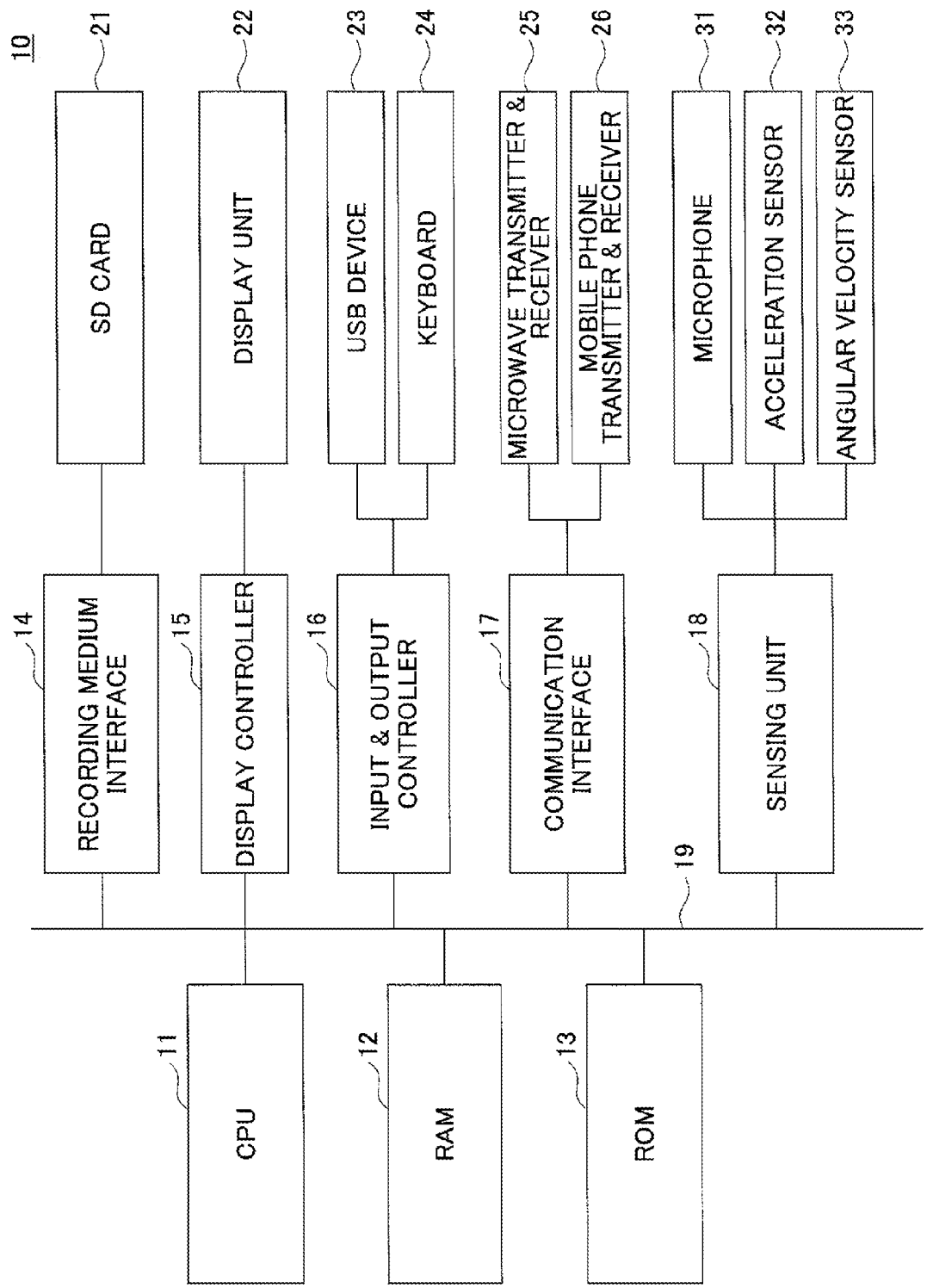
FIG. 2 is a block diagram illustrating an example of a hardware configuration of the heart rate estimating apparatus in one embodiment.

FIG. 2 is a block diagram illustrating an example of a hardware configuration of the heart rate estimating apparatus in one embodiment. In the example illustrated in FIG. 2, the heart rate estimating apparatus is built into a mobile phone which is an example of an electronic apparatus.

As illustrated in FIG. 2, a mobile phone 10 includes a CPU (Central Processing Unit) 11, a RAM (Random Access Memory) 12, a ROM (Read Only Memory) 13, a recording medium interface 14, a display controller 15, an input and output controller 16, a communication interface 17, and a sensing unit 18 that are connected via a bus 19. A recording medium, such as an SD (Secure Digital) card (or memory card) 21, may be connected to the recording medium interface 14. A display unit 22 may be connected to the display controller 15. Input and output devices may be connected to the input and output controller 16. In this example, the input and output devices may include an USB (Universal Serial Bus) device 23 and a keyboard 24. However, the input and output devices are not limited to the USB device 23 and the keyboard 24, and may include a touchscreen panel, a speaker, and the like. In a case in which the functions of the display unit 22 and the keyboard 24 are realized by a touchscreen panel, the display unit 22 and the keyboard 24 may be omitted.

A communication unit at least including a microwave transmitter and receiver 25 may be connected to the communication interface 17. In this example, the electronic apparatus is formed by the mobile phone 10, and thus, the communication unit includes a mobile phone transmitter and receiver 26. The communication unit may include a NFC (Near Field Communication) unit, a BLUETOOTH (registered trademark) communication unit, a Wi-Fi (Wireless-Fidelity) transmitter and receiver, an infrared transmitter and receiver, and the like. At least one sensor for detecting the movement of the subject 5 may be connected to the sensing unit 18. In this example, the sensors for detecting the movement of the subject 5 may include a microphone 31, an acceleration sensor 32, and an angular velocity sensor (or gyro sensor or gyroscope) 33. The microphone 31 is an example of a sound pressure sensor (or detector). The acceleration sensor 32 and the angular velocity sensor 33 are an example of a velocity sensor (or detector). Sensors, such as a pressure sensor, a temperature and humidity sensor, an illuminance sensor, a camera, and the like, may further be connected to the sensing unit 18.

The CPU 11 may include a function to control the operation of the entire mobile phone 10. The RAM 12 and the ROM 13 may form a storage unit to store programs to be executed by the CPU 11 and various data. The programs may include a program which, when executed by a computer, such as the CPU 11, causes the computer to function as a heart rate estimating apparatus. The storage unit may include the SD card 21. The storage unit that stores one or more programs is an example of a non-transitory computer-readable storage medium.

The display unit 22 may include a function to display results of a heart rate estimating process, operation screens (or menus), and the like under control of the display controller 15. The results of the heart rate estimating process and the like, output under control of the input and output controller 16, may be output to the USB device 23. The USB device 23 may be formed by a USB cable, a USB memory, and the like, for example. The keyboard 24 may be operated when inputting various commands, data, and the like to the mobile phone 10 via the input and output controller 16.

Figure 3:
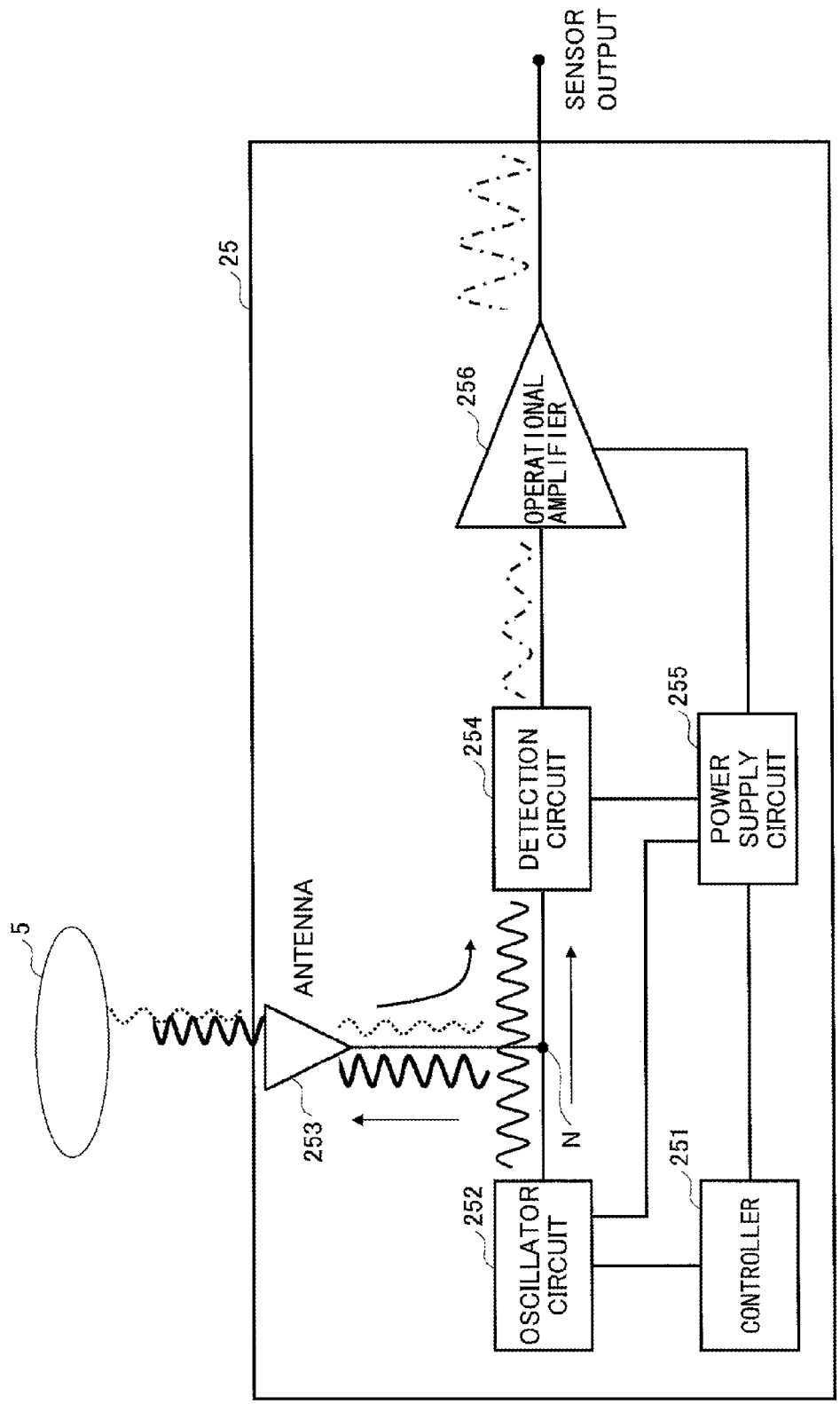
FIG. 3 is a block diagram illustrating an example of a microwave transmitter and receiver.

FIG. 3 is a block diagram illustrating an example of the microwave transmitter and receiver 25. The microwave transmitter and receiver 25 illustrated in FIG. 3 may include a controller 251, an oscillator circuit 252, an antenna 253, a detection circuit 254, a power supply circuit 255, and an operational amplifier 256. Transmitting wave (that is, microwave) generated by the oscillator circuit 252 may branch to the antenna 253 and the detection circuit 254, and the subject 5 may be irradiated with the transmitting wave transmitted from the antenna 253. The transmitting wave reaching the subject 5 may be reflected, and the antenna 253 may receive the reflected wave of the transmitted wave, reflected from the subject 5. The reflected wave received by the antenna, indicated by a dotted line, and the transmitted wave indicated by a solid line may interfere with each other at a node N, and a combined wave (that is, DC component) indicated by a one-dot chain line may be output from the detection circuit 254. The operational amplifier 256 may amplify a predetermined frequency band of the combined wave to obtain a sensor output, and provide the sensor output to the CPU 11 via the communication interface 17. The power supply circuit 255 may include a battery to supply a power supply voltage to the controller 251, the oscillator circuit 252, the detection circuit 254, and the operational amplifier 256. For example, the battery of the power supply circuit 255 may be formed by a rechargeable battery. Of course, the power supply circuit 255 may be externally connected with respect to the microwave transmitter and receiver 25.

In the example illustrated in FIG. 3, the microwave transmitter 1 may include at least the oscillator circuit 252 and the antenna 253, and the microwave receiver 2 may include at least the antenna 253, the detection circuit 254, and the operational amplifier 256.

The microphone 31 may sense sound data, and provide the sensed sound data to the CPU 11 via the sensing unit 18. The acceleration sensor 32 may sense acceleration data of the mobile phone 10, and provide the sensed acceleration data to the CPU 11 via the sensing unit 18. The angular velocity sensor 33 may sense angular velocity data of the mobile phone 10, and provide the sensed angular velocity data to the CPU 11 via the sensing unit 18.

Figure 4:
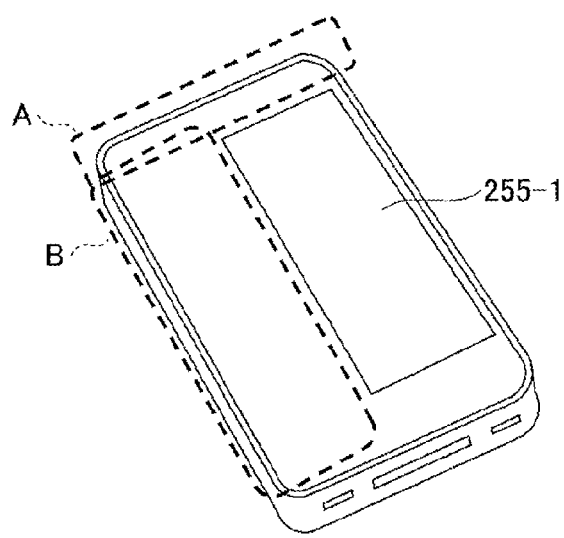
FIG. 4 is a perspective view illustrating a first example of a mobile phone with a cover on a rear side thereof removed.
Figure 5:
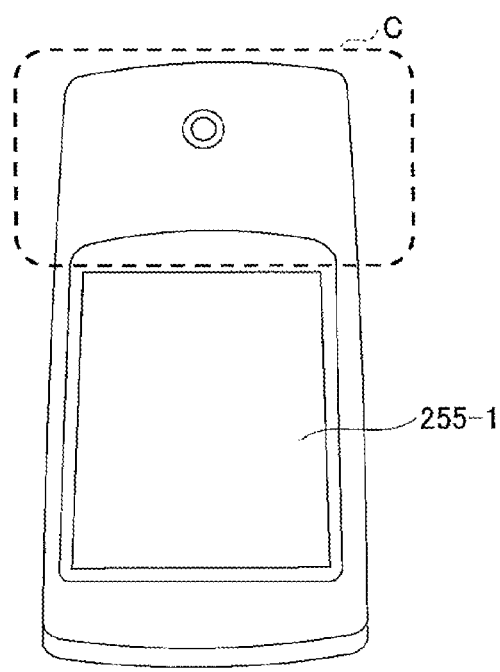
FIG. 5 is a perspective view illustrating a second example of the mobile phone with the cover on the rear side thereof removed.
Figure 6:
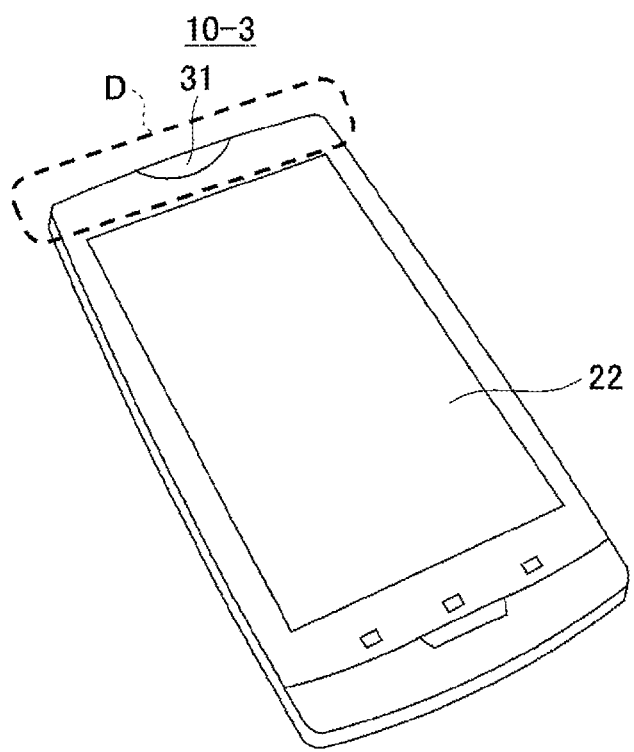
FIG. 6 is a perspective view illustrating a front side of a third example of the mobile phone.

FIGS. 4 through 6 are diagrams for explaining examples of an arrangement of the microwave transmitter and receiver 25.

FIG. 4 is a perspective view illustrating a first example of the mobile phone with a cover on a rear side thereof removed. In the first example illustrated in FIG. 4, the microwave transmitter and receiver 25 may be arranged in an upper region A or a side region B on a rear side of a mobile phone 10-1, excluding a region in which a battery 255-1 is arranged. Because the regions A and B do not include the region in which the battery 255-1 is arranged, it may be possible to prevent the microwave transmission and reception from being blocked by the battery 255-1 and deteriorating the quality of the microwave transmission and reception. In addition, because the regions A and B are provided on the back side of the mobile phone 10-1, on the opposite side from a front side of the mobile phone 10-1 provided with the display unit 22 and the keyboard 24 (or touchscreen panel), it may be possible to prevent the microwave transmission and reception from being blocked by the display unit 22 and the keyboard 24 (or touchscreen panel) and deteriorating the quality of the microwave transmission and reception. For example, in a case in which the mobile phone 10-1 is used in a state where the subject 5 wears the mobile phone 10-1 using a belt or the like, or places the mobile phone 10-1 within a pocket of the clothing, so that the back side of the mobile phone 10-1 faces the breast, arm or the like of the subject 5, the display unit 22 and the keyboard 24 (or touchscreen panel) provided on the front side of the mobile phone 10-1 are visible by the subject 5. Hence, the operability of the mobile phone 10-1 (that is, heart rate estimating apparatus) is good in that the subject 5 may operate the mobile phone 10-1 using the visible display unit 22 and the keyboard 24 (or touchscreen panel).

FIG. 5 is a perspective view illustrating a second example of the mobile phone with the cover on the rear side thereof removed. In the second example illustrated in FIG. 5, the microwave transmitter and receiver 25 may be arranged in an upper region C on a rear side of a mobile phone 10-2, excluding a region in which a battery 255-1 is arranged. Because the region C does not include the region in which the battery 255-1 is arranged, it may be possible to prevent the microwave transmission and reception from being blocked by the battery 255-1 and deteriorating the quality of the microwave transmission and reception. In addition, because the region C is provided on the back side of the mobile phone 10-2, on the opposite side from a front side of the mobile phone 10-2 provided with the display unit 22 and the keyboard 24 (or touchscreen panel), it may be possible to prevent the microwave transmission and reception from being blocked by the display unit 22 and the keyboard 24 (or touchscreen panel) and deteriorating the quality of the microwave transmission and reception. For example, in a case in which the mobile phone 10-2 is used in a state where the subject 5 wears the mobile phone 10-2 using a belt or the like, or places the mobile phone 10-2 within a pocket of the clothing, so that the back side of the mobile phone 10-2 faces the breast, arm or the like of the subject 5, the display unit 22 and the keyboard 24 (or touchscreen panel) provided on the front side of the mobile phone 10-2 are visible by the subject 5. Hence, the operability of the mobile phone 10-2 (that is, heart rate estimating apparatus) is good in that the subject 5 may operate the mobile phone 10-2 using the visible display unit 22 and the keyboard 24 (or touchscreen panel).

FIG. 6 is a perspective view illustrating a front side of a third example of the mobile phone. In the third example illustrated in FIG. 6, the microwave transmitter and receiver 25 may be arranged in an upper region D on a front side of a mobile phone 10-3, excluding regions in which the display unit 22 and the keyboard 24 (or touchscreen panel) are arranged. Because the region D does not include the regions in which the display unit 22 and the keyboard 24 (or touchscreen panel) are arranged, it may be possible to prevent the microwave transmission and reception from being blocked by the display unit 22 and the keyboard (or touchscreen panel) and deteriorating the quality of the microwave transmission and reception. For example, in a case in which the mobile phone 10-3 is used in a state where the mobile phone 10-3 is operated by the subject 5, the microwave transmitter and receiver 25 may continue the microwave transmission and reception with respect to the subject 5, and the operability of the mobile phone 10-3 (that is, heart rate estimating apparatus) is good in that the subject 5 may operate the mobile phone 10-3 using the visible display unit 22 and the keyboard 24 (or touchscreen panel).

Figure 7:
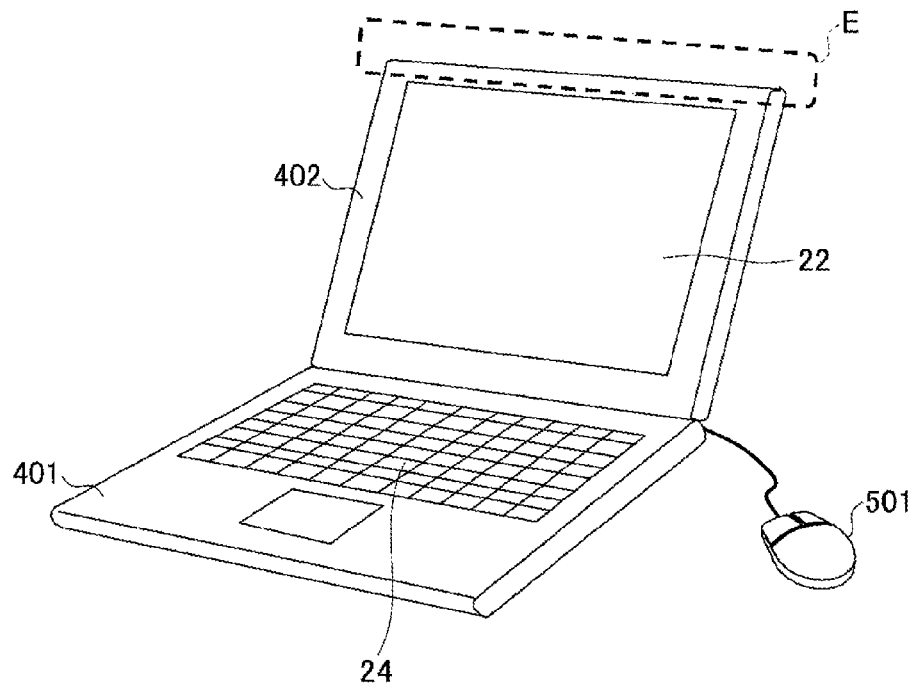
FIG. 7 is a perspective view illustrating an example of a PC (Personal Computer)
Figure 8:
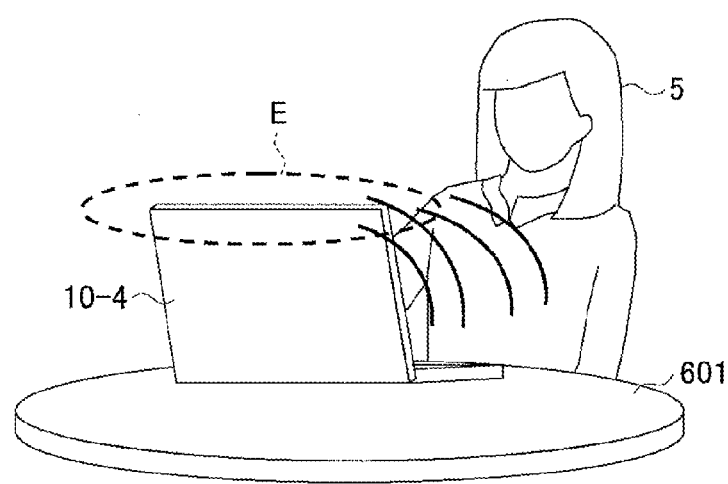
FIG. 8 is a diagram illustrating a state of use of the PC.

FIGS. 7 and 8 are diagrams for explaining a further arrangement of the microwave transmitter and receiver 25. FIG. 7 is a perspective view illustrating an example of a PC (Personal Computer), and FIG. 8 is a diagram illustrating a state of use of the PC. The PC is an example of the electronic apparatus. A PC 10-4 illustrated in FIGS. 7 and 8 may have a hardware configuration similar to that of the mobile phone 10 illustrated in FIG. 2 but excluding the mobile phone transmitter and receiver 26.

The PC 10-4 illustrated in FIG. 7 may include a main part 401 that is provided with the keyboard 24 and the like, and a lid part 402 that is provided with the display unit 22. FIG. 7 illustrates a state where the lid part 402 is open. A mouse 501 is an example of an input device connected to the input and output controller 16 within the main part 401. The microwave transmitter and receiver 25 may be arranged in an upper region E of the lid part 402 of the PC 10-4, excluding a region in which the display unit 22 is arranged. Because the region E does not include the region in which the display unit 22 is arranged, it may be possible to prevent the microwave transmission and reception from being blocked by the display unit 22 and deteriorating the quality of the microwave transmission and reception. For example, in a case in which the PC 10-4 is used in a state where the subject 5 operates the keyboard 24 of the PC 10-4 that is placed on a table 601 as illustrated in FIG. 8, the microwave transmitter and receiver 25 may continue the microwave transmission and reception with respect to the subject 5, and the operability of the PC 10-4 (that is, heart rate estimating apparatus) is good in that the subject 5 may operate the PC 10-4 using the visible display unit 22 and the keyboard 24.

Figure 9:
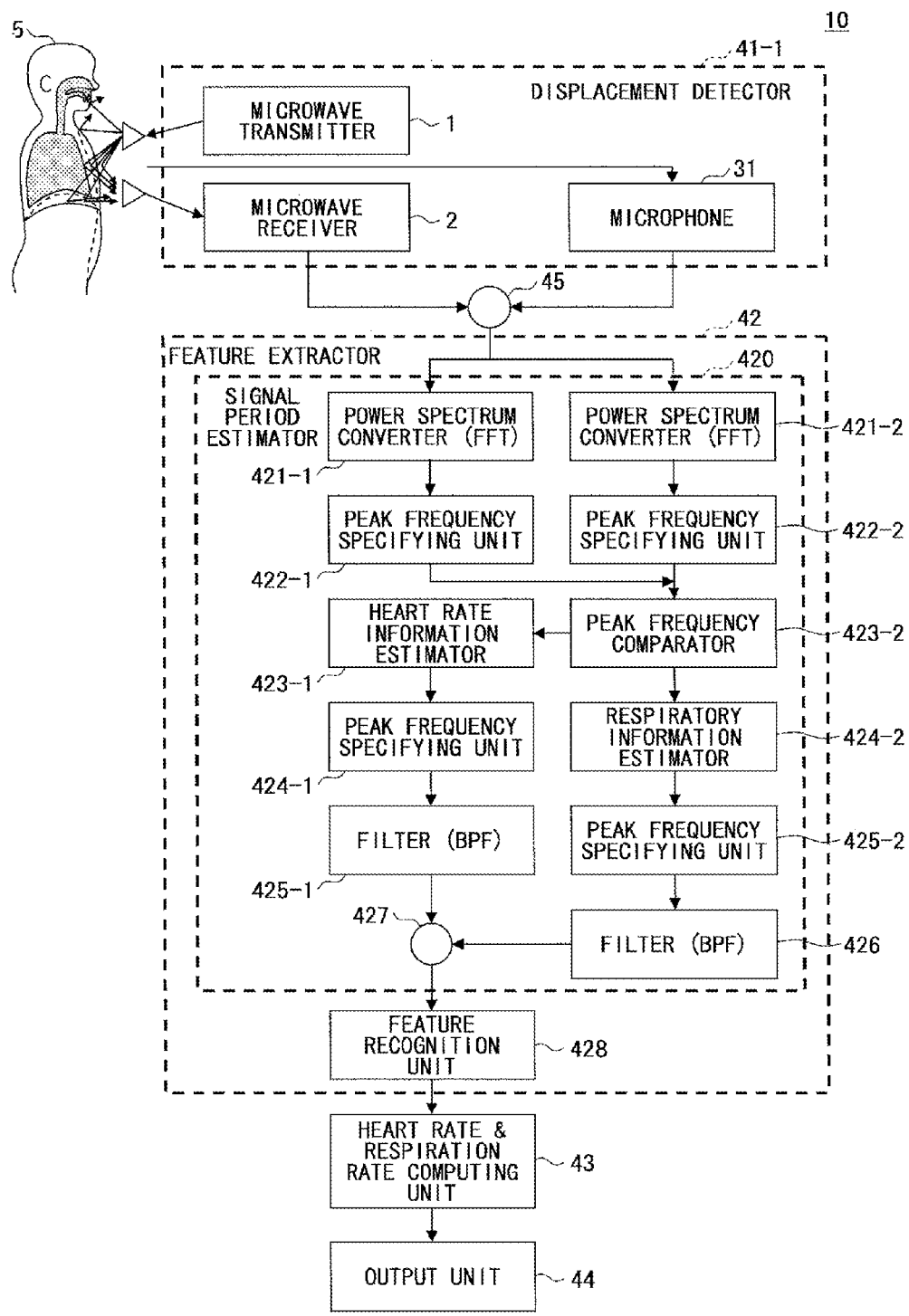
FIG. 9 is a block diagram illustrating an example of a functional configuration of the mobile phone in a case in which a microphone is used.

Next, a description will be given of the operation for a case in which the microphone 31 is used as an example of the sensor to detect the movement of the subject 5, by referring to FIG. 9. FIG. 9 is a block diagram illustrating an example of a functional configuration of the mobile phone 10 in a case in which the microphone 31 is used.

The mobile phone 10 illustrated in FIG. 9 may include a displacement detector 41-1, a feature point extractor 42, a heart rate and respiration rate computing unit 43, an output unit 44, and a data distributor 45. The data distributor 45 may form a part of the displacement detector 41-1, or form a part of the feature point extractor 42. Functions of the feature point extractor 42, the heart rate and respiration rate computing unit 43, and the output unit 44 may be realized by the CPU 11 illustrated in FIG. 2. The CPU 11 may also realize a function of the data distributor 45.

The displacement detector 41-1 may include the microwave transmitter 1, the microwave receiver 2, and the microphone 31. Data of the reflected wave from the subject 5 irradiated with the microwave transmitted from the microwave transmitter 1 and detected by the microwave receiver 2, and sound data from a vicinity of the subject 5 and sensed by the microphone 31 are separately input to the feature point extractor 42 after the data distributor 45 confirms that the data of the reflected wave (hereinafter also referred to as "reflected wave data") and the sound data include no loss. The sound data sensed by the microphone 31 may include data of sound that is generated when the subject 5 moves. The sound that is generated when the subject 5 moves may include rubbing sound of the clothing itself worn by the subject 5, rubbing sound of the clothing making contact with a chair, a seat belt of a vehicle, and the like, sound of shoes of the subject 5 making contact with a floor and the like when the subject 5 walks, and the like. The reflected wave data output from the microwave receiver 2 and the sound data output from the microphone 31 may be input directly to the feature point extractor 42, and in this case, the data distributor 45 may be omitted.

The feature point extractor 42 may include a signal period estimator 420 and a feature recognition unit 428. The signal period estimator 420 may include power spectrum converters 421-1 and 421-2, peak frequency specifying units 422-1 and 422-2, a heart rate information estimator 423-1, a peak frequency comparator 423-2, a peak frequency specifying unit 424-1, a respiratory information estimator 424-2, a filter 425-1, a peak frequency specifying unit 425-2, a filter 426, and an adder 427. The power spectrum converters 421-1 and 421-2 are examples of first and second frequency analyzers.

Figure 10:
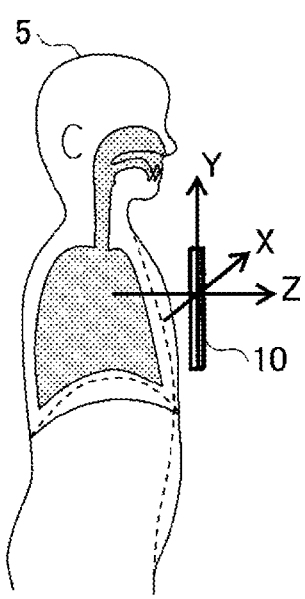
FIG. 10 is a diagram illustrating a relationship between a subject and XYZ coordinate axes.
Figure 11:
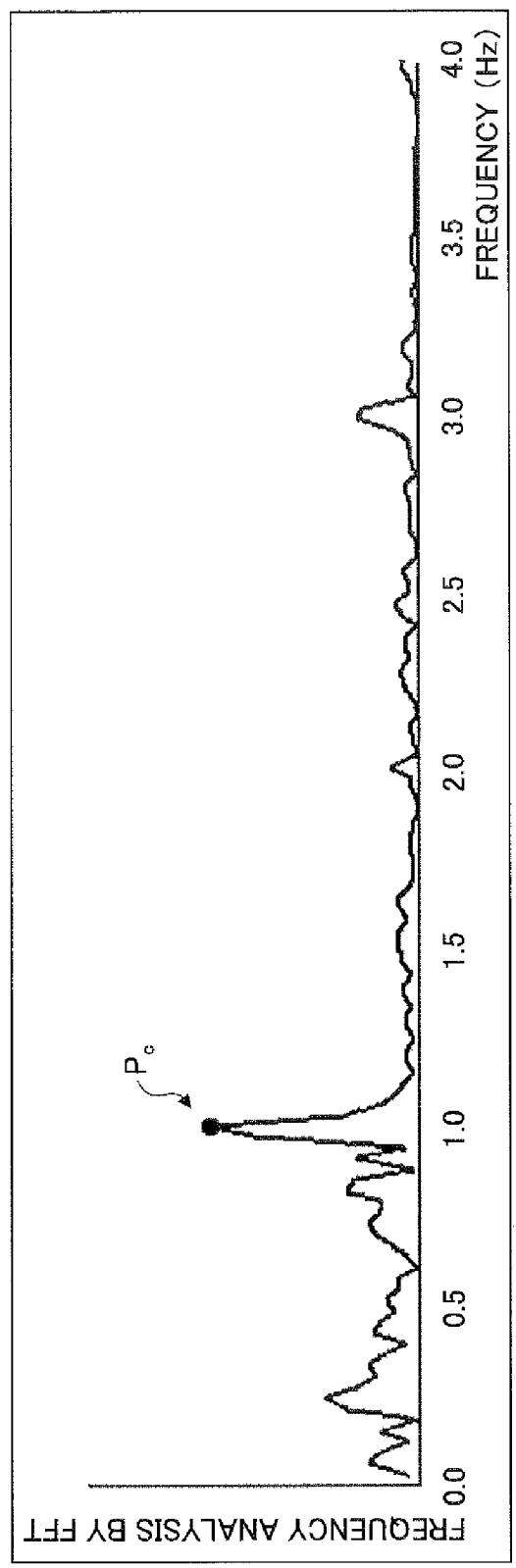
FIG. 11 is a diagram illustrating an example of an analysis result obtained by frequency analysis of measured results from a contact type heart rate measuring apparatus.

FIG. 10 is a diagram illustrating a relationship between the subject 5 and XYZ coordinate axes. FIG. 11 is a diagram illustrating an example of an analysis result obtained by frequency analysis of measured results from a contact type heart rate measuring apparatus using an ear clip.

Figure 12:
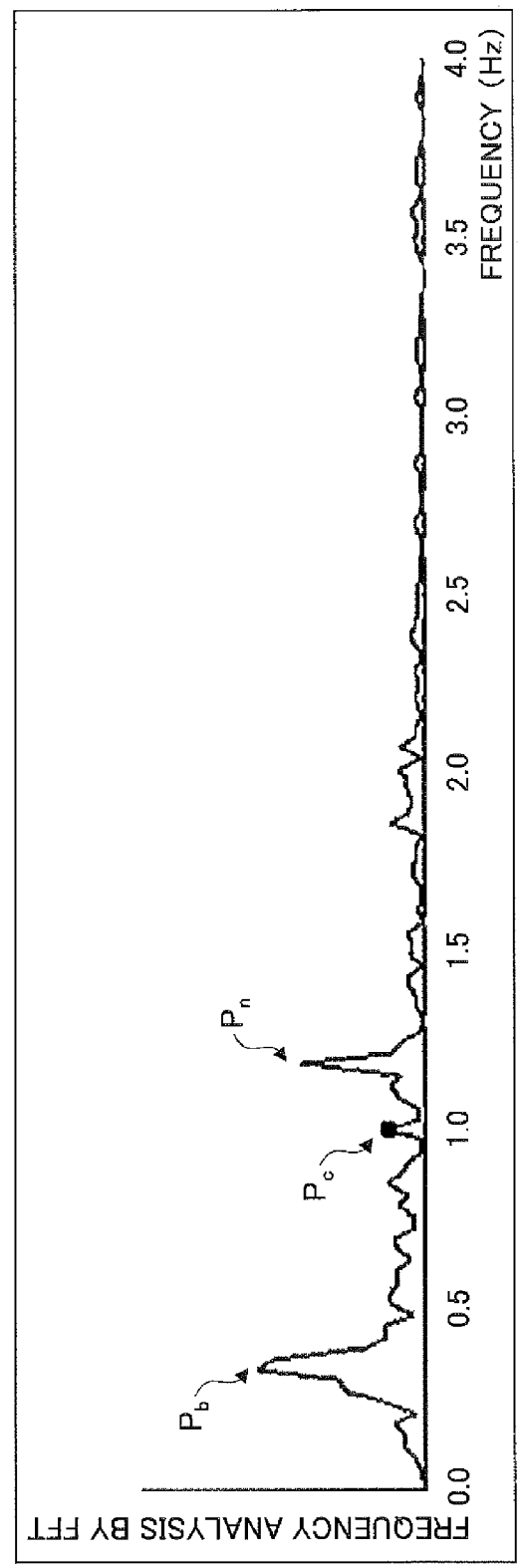
FIG. 12 is a diagram illustrating an example of an analysis result obtained by frequency analysis of detected result of reflected wave from the subject irradiated with microwave.

The power spectrum converter 421-1 may convert a power spectrum by frequency analysis of the reflected wave data detected by the microwave receiver 2. In this example, FFT (Fast Fourier Transform) is used for the frequency analysis, and an analysis result illustrated in FIG. 12 may be obtained, for example. FIG. 12 is a diagram illustrating an example of the analysis result obtained by frequency analysis of detected result of the reflected wave data from the subject 5 irradiated with the microwave. FIG. 12 illustrates the analysis result that is obtained simultaneously as the measurement to obtain the analysis result illustrated in FIG. 11, for example. The peak frequency specifying unit 422-1 may specify, from the analysis result illustrated in FIG. 12, the frequency at which a peak greater than or equal to a predetermined amplitude is generated.

Figure 13:
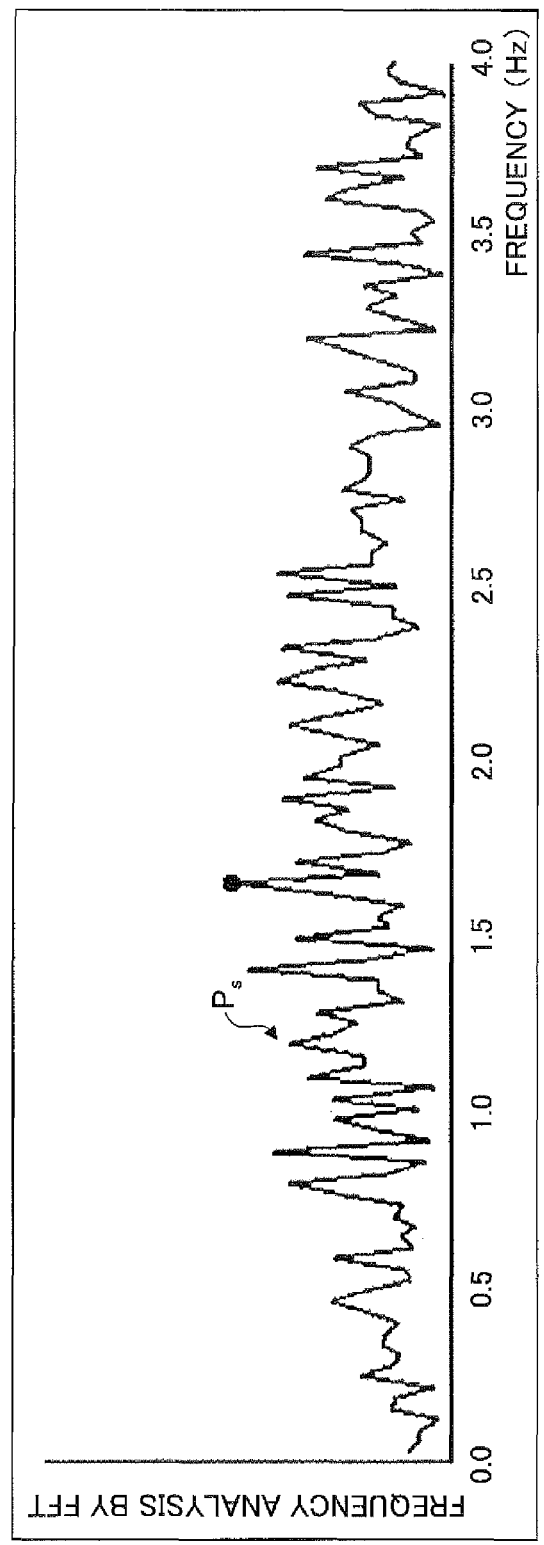
FIG. 13 is a diagram illustrating an example of an analysis result obtained by frequency analysis of sensed result from the microphone.

On the other hand, the power spectrum converter 421-2 may convert a power spectrum by frequency analysis of the sound data sensed by the microphone 31. In this example, the FFT is used for the frequency analysis, and an analysis result illustrated in FIG. 13 may be obtained, for example. FIG. 13 is a diagram illustrating an example of the analysis result obtained by frequency analysis of sensed result from the microphone 31. The peak frequency specifying unit 422-2 may specify, from the analysis result illustrated in FIG. 13, the frequency at which a peak greater than or equal to a predetermined amplitude is generated.

The peak frequency comparator 423-2 may compare the frequencies (hereinafter also referred to as "peak frequencies") at which the peaks specified by the peak frequency specifying units 422-1 and 422-2 are generated, and input a compared result to the heart rate information estimator 423-1. The heart rate estimator 423-1 may search the peak frequency in a frequency range of 0.5 Hz or higher and 4.0 Hz or lower, for example, in order to estimate the heart rate information. The heart rate estimator 423-1 may exclude, from the heart rate candidates, the peak frequency located in a vicinity (that is, within a predetermined frequency range) of the peak frequencies illustrated in FIG. 13, amongst the peak frequencies illustrated in FIG. 12. As illustrated in FIG. 11, a correct peak Pc corresponding to the heart beat is located in a vicinity of 1.0 Hz. On the other hand, as illustrated in FIG. 12, according to the frequency analysis result obtained from the detected result of the reflected wave, the peak Pc in the vicinity of 1.0 Hz and a peak Pn in a vicinity of 1.2 Hz exist. However, as illustrated in FIG. 13, according to the frequency analysis result obtained from the sensed result of the sound data from the microphone 31, no peak exists in the vicinity of 1.0 Hz, and a peak Ps exists in a vicinity of 1.2 Hz. Hence, it may be seen that the peak Pn in FIG. 12 is due to noise. In other words, the compared result from the peak frequency comparator 423-2 may indicate that the peak Pn illustrated in FIG. 12 and the peak Ps illustrated in FIG. 13 exist in the vicinity of 1.2 Hz, and the heart rate information estimator 423-1 may exclude the peak Pn from the heart rate candidates.

The peak frequency specifying unit 424-1 may specify the frequency (that is, peak frequency) of the peak, excluding the peak Pn that is excluded from the heart rate candidates by the heart rate information estimator 423-1. The filter 425-1 may perform a filter process with respect to the reflected wave data, about the peak frequency specified as the heart rate candidate, that is, using the peak frequency specified as the heart rate candidate as a center of the filter process. In this example, the filter process may be a BPF (Band-Pass Filter) process, in order to accurately extract the heart rate that may fluctuate for each heart beat. The reflected wave data subjected to the filter process of the filter 425-1 may be input to the feature recognition unit 428 via the adder 427.

In this example, a respiration rate estimating process to estimate the respiration rate is performed in addition to the heart rate estimating process to estimate the heart rate. For this reason, the compared result from the peak frequency comparator 423-2 may be input to the respiratory information estimator 424-2. The respiratory information estimator 424-2 may search the peak frequency in a frequency range of 0.1 Hz or higher and 0.8 Hz or lower, for example, in order to estimate the respiratory information. Amongst the peak frequencies illustrated in FIG. 12, the respiratory information estimator 424-2 may regard, as a respiratory candidate, a peak Pb greater than or equal to a predetermined amplitude in a frequency range of 0.1 Hz or higher and 0.8 Hz or lower. In this example, between the respiratory information and the heart rate information to be processed by the power spectrum converters 422-1 and 422-2, the amount of respiratory information to be processed is set to be several times larger than the amount of heart rate information to be processed, for example.

The peak frequency specifying unit 425-2 may specify the frequency of the peak Pb (peak frequency: in a vicinity of 0.3 Hz) that becomes the respiratory candidate and is extracted by the respiratory information estimator 424-2. The filter 426 may perform a filter process with respect to the reflected wave data, about the frequency of the peak Pb (peak frequency) specified as the respiratory candidate, that is, using the peak frequency specified as the respiratory candidate as a center of the filter process. In this example, the filter process may be a BPF process, in order to accurately extract the respiration rate that may fluctuate for each breath. The reflected wave data subjected to the filter process of the filter 426 may be input to the feature recognition unit 428 via the adder 427.

In FIG. 12, a relatively large peak exists in a frequency range lower than 0.8 Hz. However, this relatively large peak may be regarded as being caused by the subject 5 feeling tension at the start of the heart rate estimation, and the rise in the heart rate from that in a resting state due to the tension may be approximately 20%. Accordingly, in the case in which the relatively large peak occurs due to tension felt by the subject 5, low-frequency components lower than 0.8 Hz, for example, may be ignored in FIG. 12, in order to utilize, for the heart rate estimation, the analysis result in the frequency range of 0.8 Hz or higher and 4.0 Hz or lower in which the general heart rate falls.

The feature recognition unit 428 recognizes the feature points of the data received from the filter 425-1 and the feature points of the data received from the filter 426, by a known method. More particularly, the feature recognition unit 428 may acquire a heart beat interval (or pitch) by subjecting the output data of the filter 425-1 to a first order differentiation in order to obtain the feature points, and acquire a respiration interval (or pitch) by subjecting the output data of the filter 426 to a first order differentiation in order to obtain the feature points.

The heart rate and respiration rate computing unit 43 may compute the heart rate from the heart beat interval output from the feature recognition unit 428, and compute the respiration rate from the respiration interval output from the feature recognition unit 428. The output unit 44 may output the heart rate and the respiration rate computed by the heart rate and respiration rate computing unit 43. The heart rate and the respiration rate computed by the heart rate and respiration rate computing unit 43 may be stored in a storage unit.

When not computing the respiration rate, the respiratory information estimator 424-2, the peak frequency specifying unit 425-2, the filter 426, and the adder 427 may be omitted. In this case, a heart rate computing unit may be provided in place of the heart rate and respiration rate computing unit 43.

Figure 14:
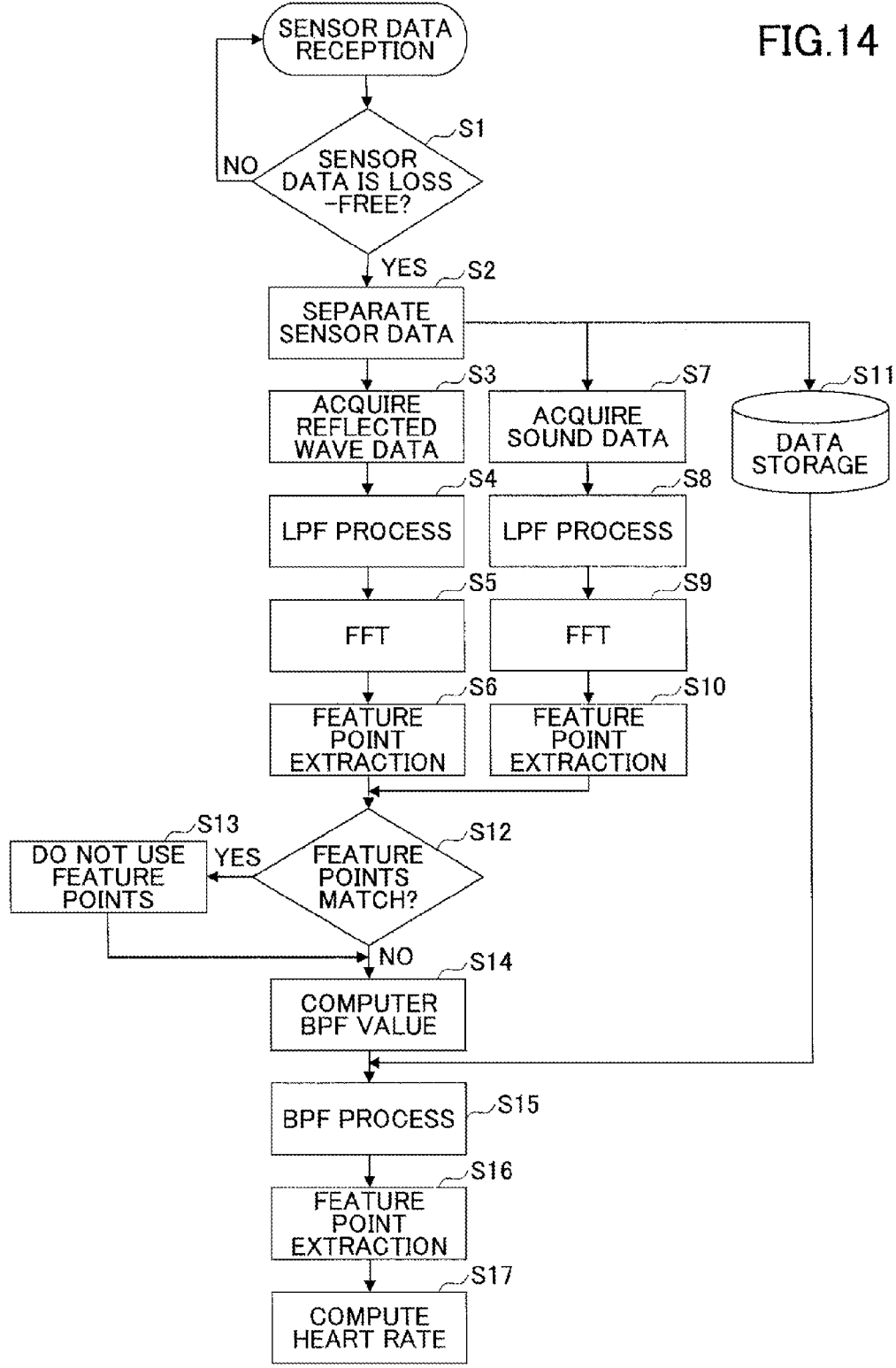
FIG. 14 is a flow chart for explaining an example of a heart rate estimating process.

FIG. 14 is a flow chart for explaining an example of the heart rate estimating process. The heart rate estimating process illustrated in FIG. 14 may be executed by the CPU 11 illustrated in FIG. 2, or by functional blocks including the power spectrum converters 421-1 and 421-2, the peak frequency specifying units 422-1 and 422-2, the heart rate information estimator 423-1, the peak frequency comparator 423-2, and the peak frequency specifying unit 424-1 illustrated in FIG. 9.

The heart rate estimating process illustrated in FIG. 14 may be started when the detected result from the microwave receiver 2 is input via the communication interface 17 and the sensed result from the microphone 31 is input via the sensing unit 18. In FIG. 14, step S1 checks the input sensor data, including the detected result and the sensed result, and decides whether the sensor data are loss-free (that is, includes no loss). The process advances to step S2 when the sensor data are loss-free and the decision result in step S1 becomes YES. Step S2 separates the sensor data into the detected result of the reflected wave data detected by the microwave receiver 2, and the sensed result of the sound data sensed by the microphone 31. Step S11 stores the reflected wave data and the sound data, separated in step S2, in the storage unit.

Step S3 acquires the reflected wave data, and step S4 subjects the acquired reflected data to a LPF (Low-Pass Filter) process in order to limit the peak frequency to be searched to a frequency range of 5 Hz or lower, for example. Step S5 subjects the reflected wave data that are subjected to the LPF process to a FFT that is an example of the frequency analysis. Step S6 extracts the feature points from the frequency analysis result of the reflected wave data that are subjected to the LPF process, and the process advances to step S12.

On the other hand, step S7 acquires the sound data, and step S8 subjects the acquired sound data to a LPF process in order to limit the peak frequency to be searched to a frequency range of 5 Hz or lower, for example, similarly to step S4. Step S9 subjects the sound data that are subjected to the LPF process to a FFT that is an example of the frequency analysis. Step S10 extracts the feature points from the frequency analysis result of the sound data that are subjected to the LPF process, and the process advances to step S12.

Step S12 decides whether a feature point extracted in step S6 matches a feature point extracted in step S10. When matching feature points exist and the decision result in step S10 is YES, step S13 excludes the matching feature points from the heart rate candidates, by not using the matching feature points. After step S13 or when the decision result in step S12 is NO, step S14 computes a BPF value to be used by a BPF process that is performed in order to accurately extract the heart rate that may fluctuate for each heart beat. In addition, step S15 uses the BPF value computed in step S14, in order to perform the BPF process on the reflected wave data stored in the storage unit in step S11, about the feature point (peak frequency) extracted as the heart rate candidate, that is, using the peak frequency specified as the heart rate candidate as a center of the BPF process.

Step S16 acquires the heart beat interval by performing a first order differentiation on the reflected wave data that are subjected to the BPF process in step S15 in order to obtain the feature points. Step S17 computes the heart rate from the heart beat interval acquired in step S16.

Figure 15:
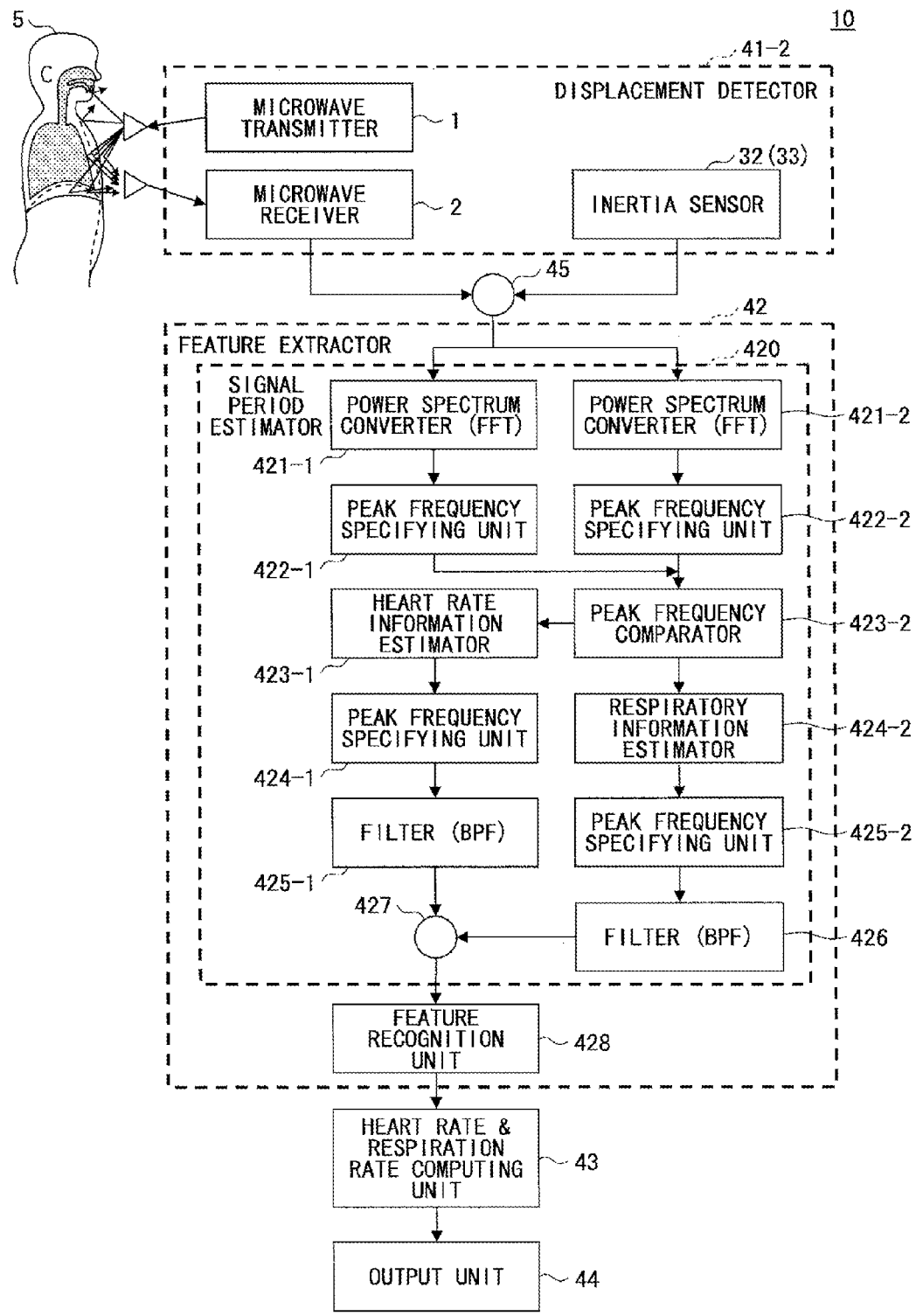
FIG. 15 is a block diagram illustrating an example of a functional configuration of the mobile phone in a case in which an acceleration sensor is used.

Next, a description will be given of the operation for a case in which the acceleration sensor 32 is used as an example of the sensor to sense the movement of the subject 5, by referring to FIG. 15. FIG. 15 is a block diagram illustrating an example of a functional configuration of the mobile phone 10 in the case in which the acceleration sensor 32 is used. In FIG. 15, those parts that are the same as those corresponding parts in FIG. 9 are designated by the same reference numerals, and a description thereof will be omitted. In this example, an inertia sensor illustrated in FIG. 15 is formed by the acceleration sensor 32.

Figure 16:
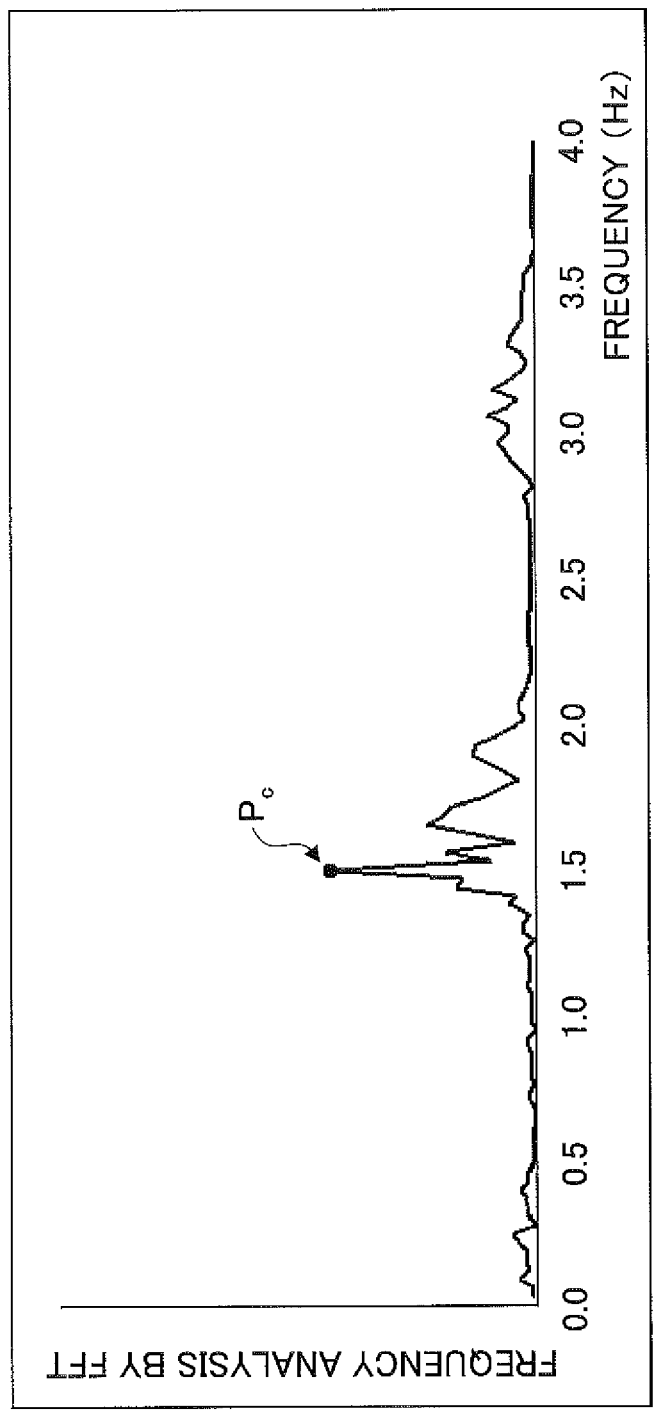
FIG. 16 is a diagram illustrating an example of an analysis result obtained by frequency analysis of measured results from the contact type heart rate measuring apparatus.

The relationship between the subject 5 and the XYZ coordinate axes is as illustrated in FIG. 10. FIG. 16 is a diagram illustrating an example of an analysis result obtained by frequency analysis of measured results from the contact type heart rate measuring apparatus using the ear clip.

Figure 17:
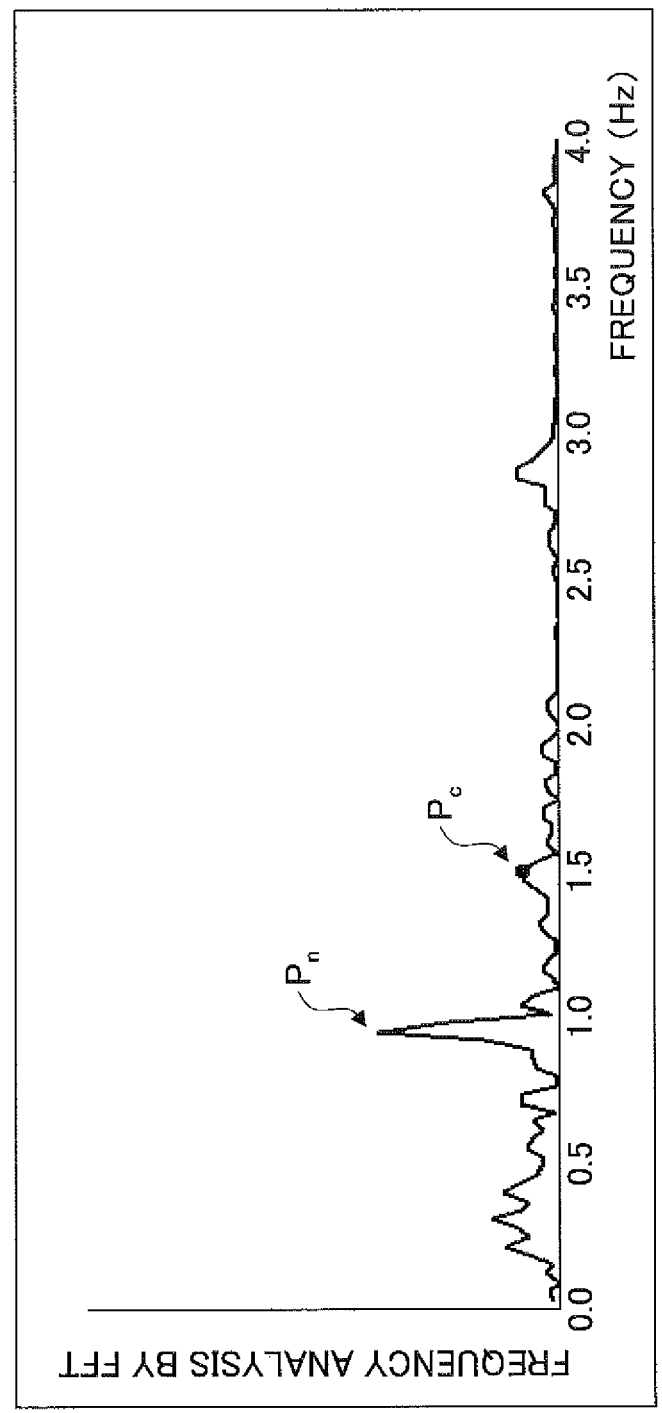
FIG. 17 is a diagram illustrating an example of an analysis result obtained by frequency analysis of detected result of reflected wave from the subject irradiated with the microwave.

The power spectrum converter 421-1 may convert a power spectrum by frequency analysis of the reflected wave data detected by the microwave receiver 2. In this example, FFT is used for the frequency analysis, and an analysis result illustrated in FIG. 17 may be obtained, for example. FIG. 17 is a diagram illustrating an example of the analysis result obtained by frequency analysis of detected result of the reflected wave data from the subject 5 irradiated with the microwave. FIG. 17 illustrates the analysis result that is obtained simultaneously as the measurement to obtain the analysis result illustrated in FIG. 16, for example. The peak frequency specifying unit 422-1 may specify, from the analysis result illustrated in FIG. 17, the frequency at which a peak greater than or equal to a predetermined amplitude is generated.

Figure 18:
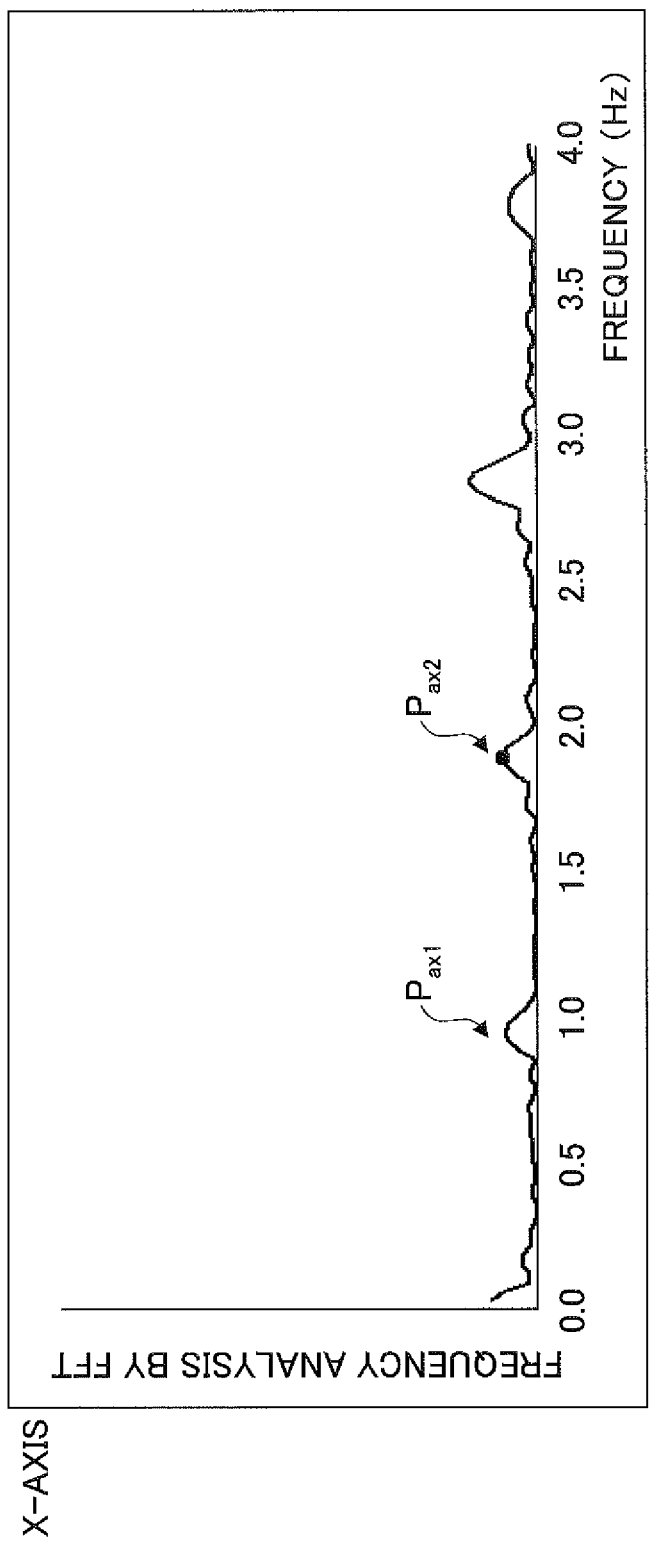
FIG. 18 is a diagram illustrating an example of an analysis result obtained by frequency analysis of the sensed results for an X-axis of the acceleration sensor.
Figure 19:
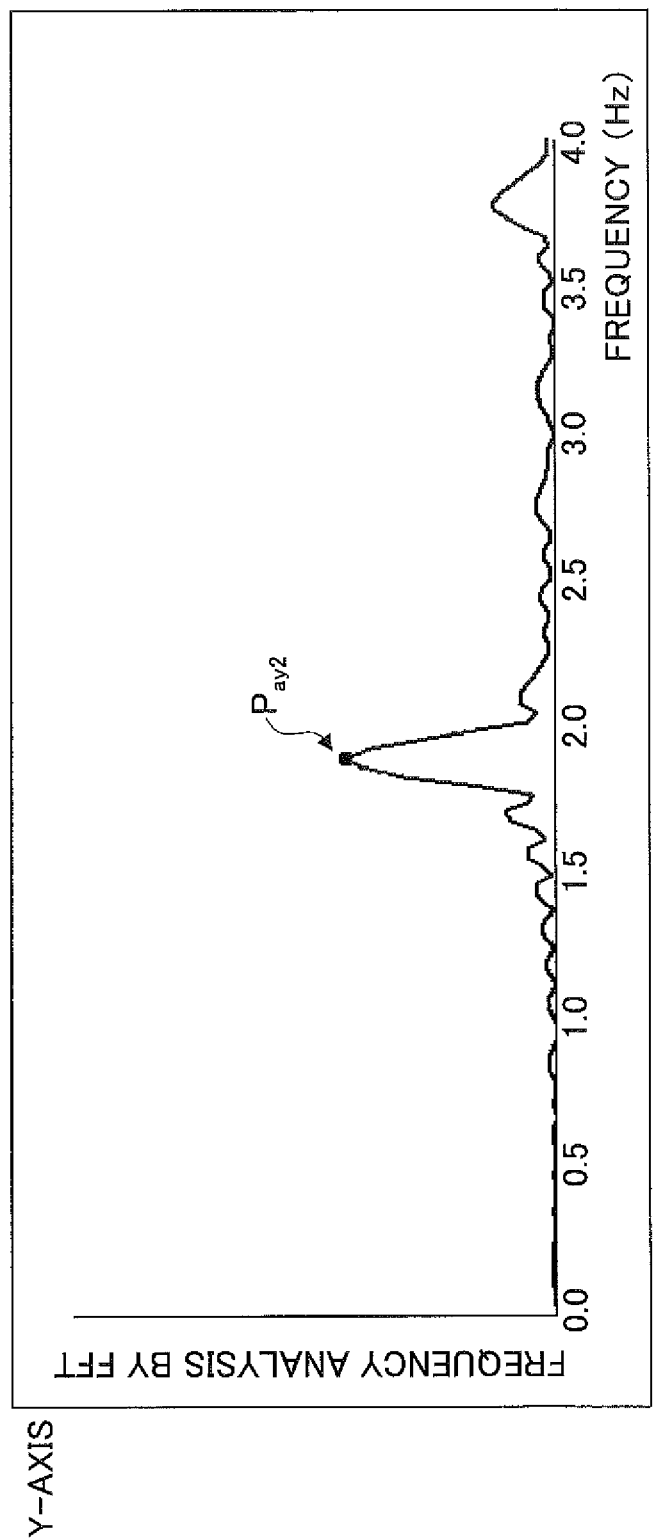
FIG. 19 is a diagram illustrating an example of an analysis result obtained by frequency analysis of the sensed results for a Y-axis of the acceleration sensor.
Figure 20:
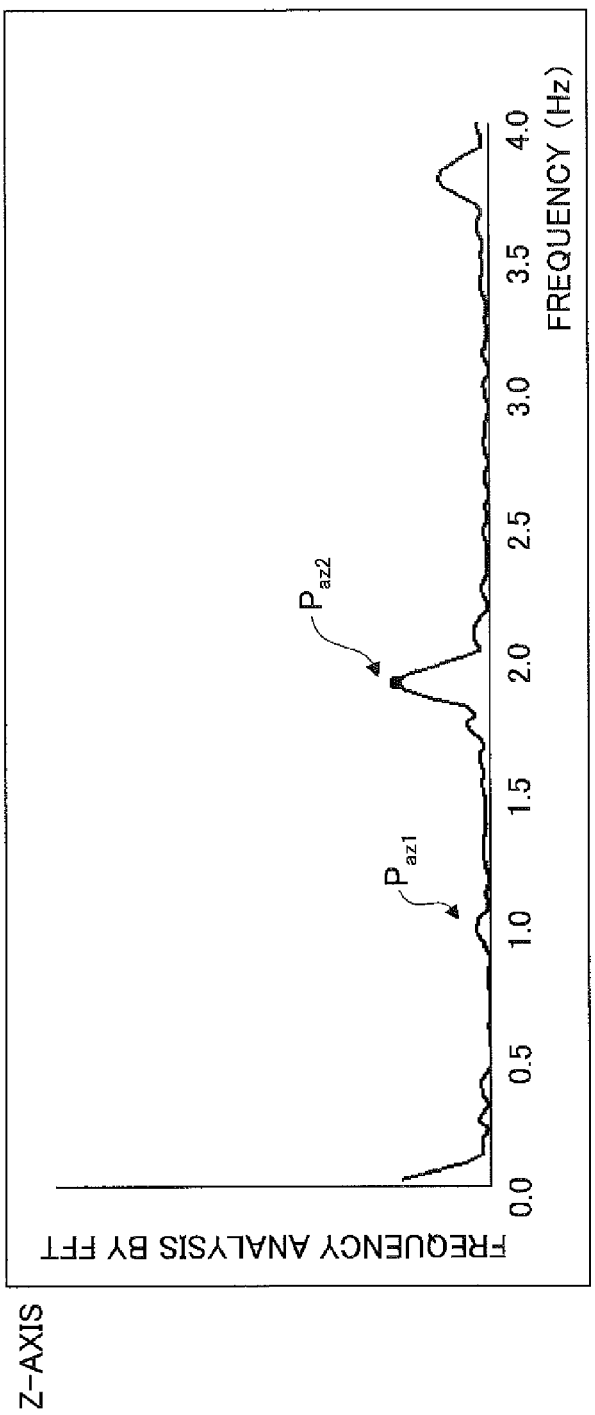
FIG. 20 is a diagram illustrating an example of an analysis result obtained by frequency analysis of the sensed results for a Z-axis of the acceleration sensor.

On the other hand, the power spectrum converter 421-2 may convert a power spectrum by frequency analysis of acceleration data sensed by the acceleration sensor 32. In this example, the FFT is used for the frequency analysis, and analysis results illustrated in FIGS. 18 through 20 may be obtained, for example. FIG. 18 is a diagram illustrating an example of the analysis result obtained by frequency analysis of the sensed results for an X-axis of the acceleration sensor 32. FIG. 19 is a diagram illustrating an example of the analysis result obtained by frequency analysis of the sensed results for a Y-axis of the acceleration sensor 32. FIG. 20 is a diagram illustrating an example of the analysis result obtained by frequency analysis of the sensed results for a Z-axis of the acceleration sensor 32. The peak frequency specifying unit 422-2 may specify, from the analysis results illustrated in FIGS. 18 through 20, the frequency at which a peak greater than or equal to a predetermined amplitude is generated.

The peak frequency comparator 423-2 may compare the frequencies (hereinafter also referred to as "peak frequencies") at which the peaks specified by the peak frequency specifying units 422-1 and 422-2 are generated, and input a compared result to the heart rate information estimator 423-1. The heart rate estimator 423-1 may search the peak frequency in a frequency range of 0.5 Hz or higher and 4.0 Hz or lower, for example, in order to estimate the heart rate information. The heart rate estimator 423-1 may exclude, from the heart rate candidates, the peak frequency located in a vicinity (that is, within a predetermined frequency range) of the peak frequencies illustrated in FIGS. 18 and 20, amongst the peak frequencies illustrated in FIG. 17. As illustrated in FIG. 16, a correct peak Pc corresponding to the heart beat is located in a vicinity of 1.5 Hz. On the other hand, as illustrated in FIG. 17, according to the frequency analysis result obtained from the detected result of the reflected wave, the peak Pc in the vicinity of 1.5 Hz and a peak Pn in a vicinity of 0.95 Hz exist. However, as illustrated in FIGS. 18 through 20, according to the frequency analysis result obtained from the sensed result of the acceleration data from the acceleration sensor 32, no peak exists in the vicinity of 1.5 Hz, and peaks Pax1 and Paz1 exist in a vicinity of 0.95 Hz. Hence, it may be seen that the peak Pn in FIG. 17 is due to noise. In other words, the compared result from the peak frequency comparator 423-2 may indicate that the peak Pn illustrated in FIG. 17 and the peaks Pax1 and Paz1 illustrated in FIGS. 18 and 20 exist in the vicinity of 0.95 Hz, and the heart rate information estimator 423-1 may exclude the peak Pn from the heart rate candidates. In this example, a peak in a vicinity of the frequencies of peaks Pax2, Pay2, and Paz2 in FIGS. 18 through 20 does not exist in the frequency analysis result obtained from the detected result of the reflected wave data illustrated in FIG. 17.

The peak frequency specifying unit 424-1 may specify the frequency (that is, peak frequency) of the peak, excluding the peak Pn that is excluded from the heart rate candidates by the heart rate information estimator 423-1. The filter 425-1 may perform a filter process with respect to the reflected wave data, about the peak frequency specified as the heart rate candidate, that is, using the peak frequency specified as the heart rate candidate as a center of the filter process. In this example, the filter process may be a BPF process, in order to accurately extract the heart rate that may fluctuate for each heart beat. The reflected wave data subjected to the filter process of the filter 425-1 may be input to the feature recognition unit 428 via the adder 427.

The process performed thereafter may be similar to that of the process illustrated in FIG. 9. In addition, the heart rate estimating process may be realized by steps similar to those illustrated in the flow chart of FIG. 14.

Next, a description will be given of the operation for a case in which the angular velocity sensor 33 is used as an example of the sensor to detect the movement of the subject 5. An example of the functional configuration of the mobile phone 10 in the case in which the angular velocity sensor 33 is used may be similar to that illustrated in FIG. 15. In this case, the inertia sensor illustrated in FIG. 15 is formed by the angular velocity sensor 33.

Figure 21:
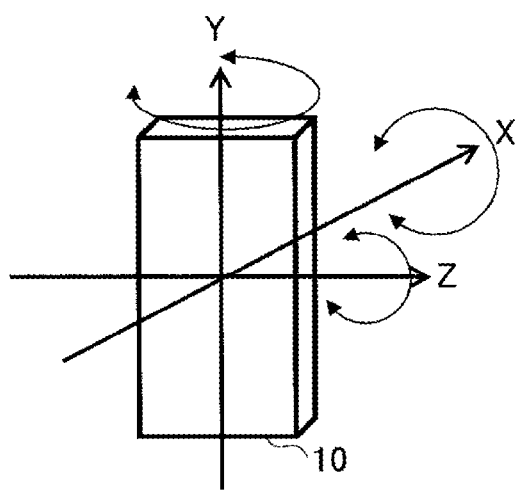
FIG. 21 is a diagram illustrating a relationship between the mobile phone and the XYZ coordinate axes.
Figure 22:
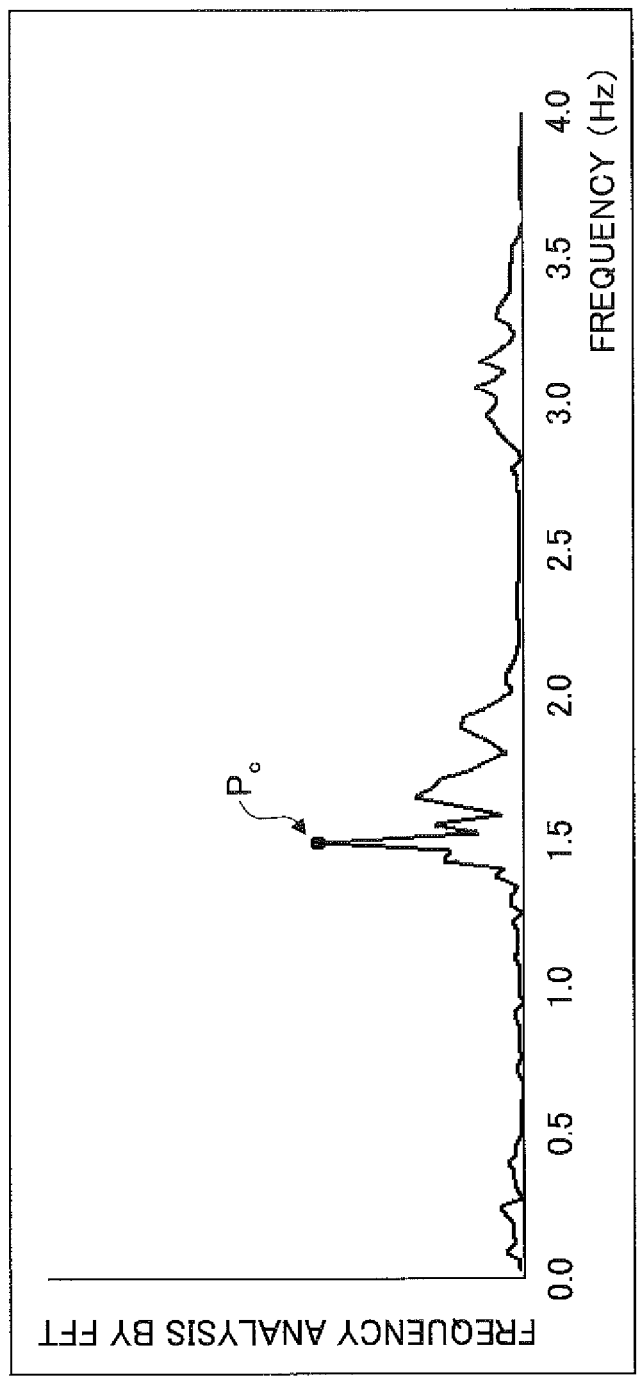
FIG. 22 is a diagram illustrating an example of an analysis result obtained by frequency analysis of measured results from the contact type heart rate measuring apparatus.

FIG. 21 is a diagram illustrating a relationship between the mobile phone 10 and the XYZ coordinate axes, and FIG. 22 is a diagram illustrating an example of an analysis result obtained by frequency analysis of measured results from the contact type heart rate measuring apparatus using the ear clip.

Figure 23:
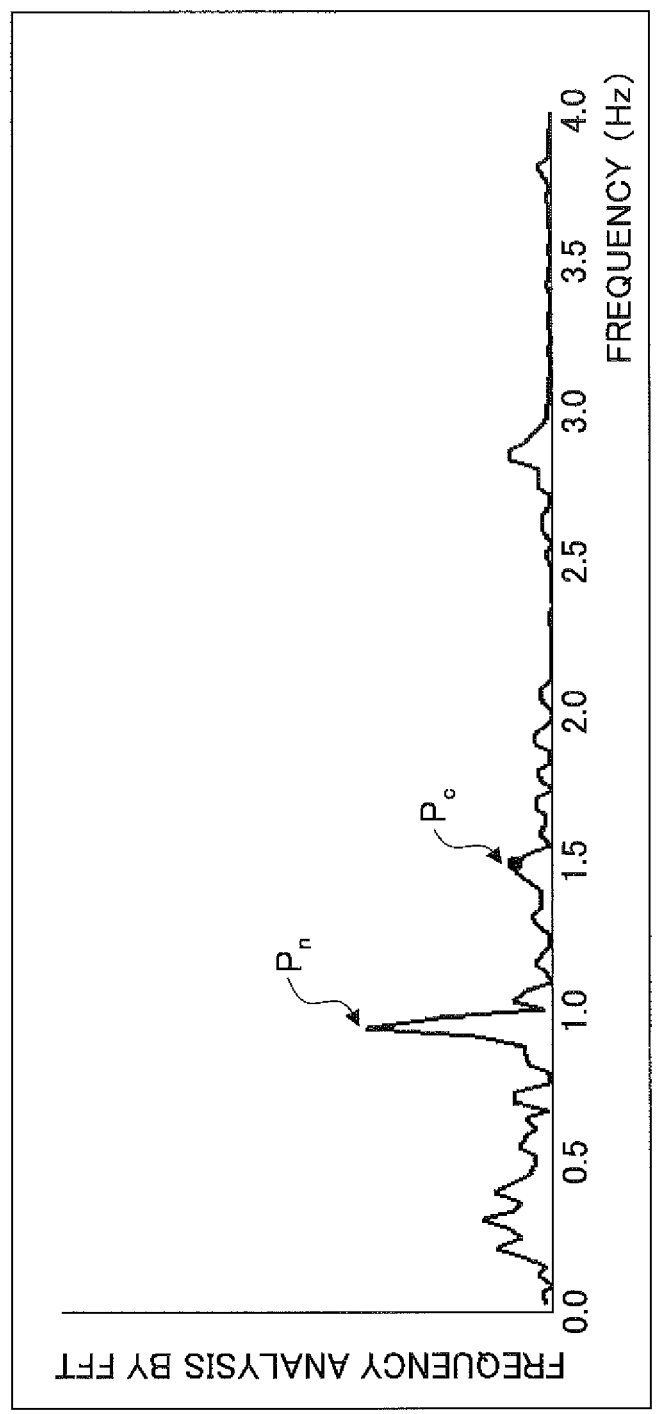
FIG. 23 is a diagram illustrating an example of an analysis result obtained by frequency analysis of detected result of reflected wave from the subject irradiated with the microwave.

The power spectrum converter 421-1 may convert a power spectrum by frequency analysis of the reflected wave data detected by the microwave receiver 2. In this example, FFT is used for the frequency analysis, and an analysis result illustrated in FIG. 23 may be obtained, for example. FIG. 23 is a diagram illustrating an example of the analysis result obtained by frequency analysis of detected result of the reflected wave data from the subject 5 irradiated with the microwave. FIG. 23 illustrates the analysis result that is obtained simultaneously as the measurement to obtain the analysis result illustrated in FIG. 22, for example. The peak frequency specifying unit 422-1 may specify, from the analysis result illustrated in FIG. 23, the frequency at which a peak greater than or equal to a predetermined amplitude is generated.

Figure 24:
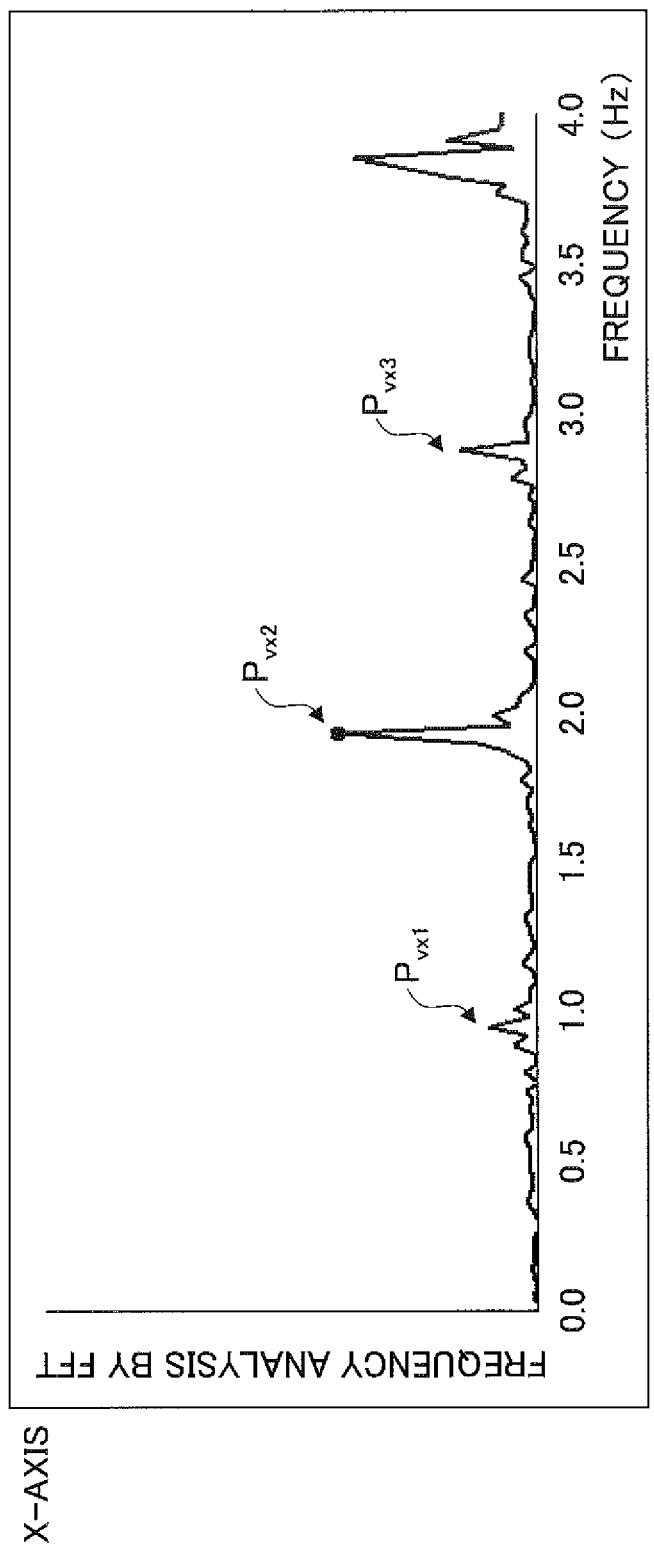
FIG. 24 is a diagram illustrating an example of an analysis result obtained by frequency analysis of the sensed results for the X-axis of the angular velocity sensor.
Figure 25:
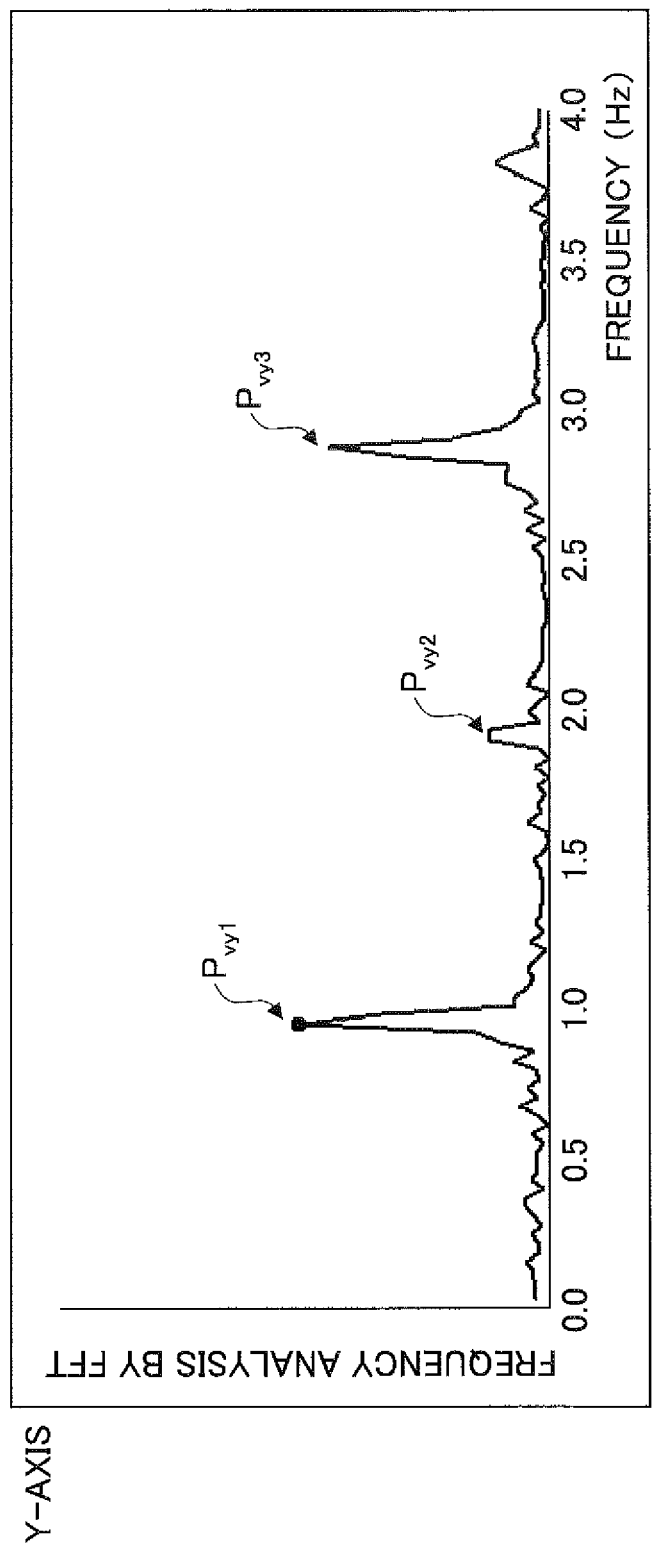
FIG. 25 is a diagram illustrating an example of an analysis result obtained by frequency analysis of the sensed results for the Y-axis of the angular velocity sensor.
Figure 26:
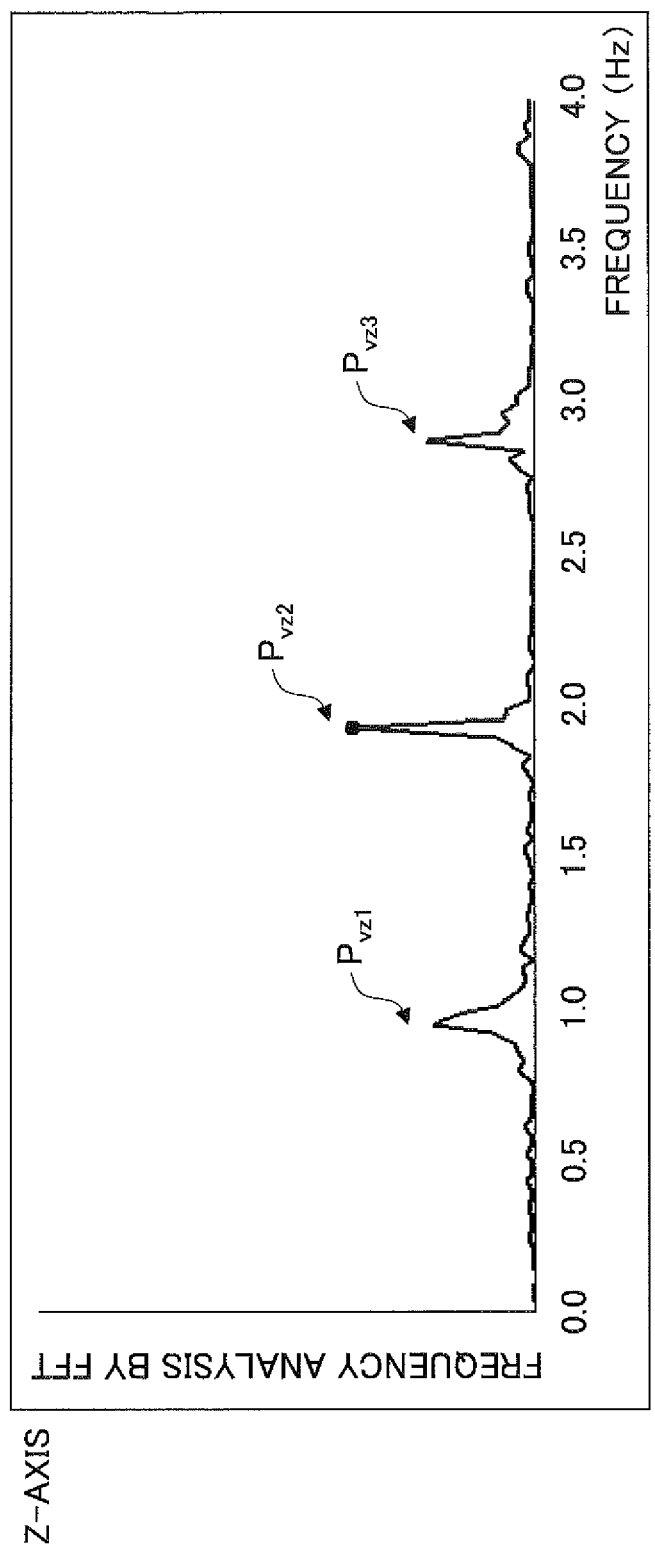
FIG. 26 is a diagram illustrating an example of an analysis result obtained by frequency analysis of the sensed results for the Z-axis of the angular velocity sensor.

On the other hand, the power spectrum converter 421-2 may convert a power spectrum by frequency analysis of angular velocity data sensed by the angular velocity sensor 33. In this example, the FFT is used for the frequency analysis, and analysis results illustrated in FIGS. 24 through 26 may be obtained, for example. FIG. 24 is a diagram illustrating an example of the analysis result obtained by frequency analysis of the sensed results for an X-axis of the angular velocity sensor 33. FIG. 25 is a diagram illustrating an example of the analysis result obtained by frequency analysis of the sensed results for a Y-axis of the angular velocity sensor 33. FIG. 26 is a diagram illustrating an example of the analysis result obtained by frequency analysis of the sensed results for a Z-axis of the angular velocity sensor 33. The peak frequency specifying unit 422-2 may specify, from the analysis results illustrated in FIGS. 24 through 26, the frequency at which a peak greater than or equal to a predetermined amplitude is generated.

The peak frequency comparator 423-2 may compare the frequencies (hereinafter also referred to as "peak frequencies") at which the peaks specified by the peak frequency specifying units 422-1 and 422-2 are generated, and input a compared result to the heart rate information estimator 423-1. The heart rate estimator 423-1 may search the peak frequency in a frequency range of 0.5 Hz or higher and 4.0 Hz or lower, for example, in order to estimate the heart rate information. The heart rate estimator 423-1 may exclude, from the heart rate candidates, the peak frequency located in a vicinity (that is, within a predetermined frequency range) of the peak frequencies illustrated in FIGS. 24 and 26, amongst the peak frequencies illustrated in FIG. 23. As illustrated in FIG. 22, a correct peak Pc corresponding to the heart beat is located in a vicinity of 1.5 Hz. On the other hand, as illustrated in FIG. 23, according to the frequency analysis result obtained from the detected result of the reflected wave, the peak Pc in the vicinity of 1.5 Hz and a peak Pn in a vicinity of 0.95 Hz exist. However, as illustrated in FIGS. 24 through 26, according to the frequency analysis result obtained from the sensed result of the angular velocity data from the angular velocity sensor 33, no peak exists in the vicinity of 1.5 Hz, and peaks Pax1, Pay1, and Paz1 exist in a vicinity of 0.95 Hz. Hence, it may be seen that the peak Pn in FIG. 23 is due to noise. In other words, the compared result from the peak frequency comparator 423-2 may indicate that the peak Pn illustrated in FIG. 23 and the peaks Pax1, Pay1, and Paz1 illustrated in FIGS. 24 and 26 exist in the vicinity of 0.95 Hz, and the heart rate information estimator 423-1 may exclude the peak Pn from the heart rate candidates. In this example, a peak in a vicinity of the frequencies of peaks Pax2, Pay2, Paz2, Pax3, Pay3, and Paz3 in FIGS. 24 through 26 does not exist in the frequency analysis result obtained from the detected result of the reflected wave data illustrated in FIG. 23.

The peak frequency specifying unit 424-1 may specify the frequency (that is, peak frequency) of the peak, excluding the peak Pn that is excluded from the heart rate candidates by the heart rate information estimator 423-1. The filter 425-1 may perform a filter process with respect to the reflected wave data, about the peak frequency specified as the heart rate candidate, that is, using the peak frequency specified as the heart rate candidate as a center of the filter process. In this example, the filter process may be a BPF process, in order to accurately extract the heart rate that may fluctuate for each heart beat. The reflected wave data subjected to the filter process of the filter 425-1 may be input to the feature recognition unit 428 via the adder 427.

The process performed thereafter may be similar to that of the process illustrated in FIG. 9. In addition, the heart rate estimating process may be realized by steps similar to those illustrated in the flow chart of FIG. 14.

A combination of frequency analysis results of sensed data from two or more sensors, amongst the microphone 31, the acceleration sensor 32, and the angular velocity sensor 33, may be used to exclude, from the heart rate candidates, the peak corresponding to the noise within the frequency analysis result that is obtained from the detected result of the reflected wave. By using the combination of the frequency analysis results of the sensed data from two or more sensors, the accuracy of extracting the peak corresponding to the noise may be improved.

According to the disclosed heart rate estimating apparatus, the heart rate estimating method, and the computer-readable storage medium, the accuracy of the heart rate estimation may be improved without requiring contact with the subject, and the estimated heart rate may be used for various purposes. For example, the health condition, sleepiness (or drowsy state), and the like of the subject may be estimated from the estimated heart rate.

A portable heart rate estimating apparatus may be a dedicated electronic apparatus that is provided with the heart rate estimating function, or may be built into an electronic apparatus that is provided with a function other than the heart rate estimating function, such as a mobile phone, a PC, and the like. By holding the portable heart rate estimating apparatus at a predetermined location within a vehicle, for example, the heart rate of a driver, who is an example of the subject, may be estimated by the heart rate estimating apparatus while the driver is riding on the vehicle. In this case, the sleepiness and the like of the driver may be estimated by a known method, for example, based on the estimated heart rate of the driver.

In addition, the heart rate estimating apparatus is not limited to the portable type apparatus, and may be fixedly set within the vehicle, for example. In this case, the heart rate of the driver, who is an example of the subject, may be estimated by the heart rate estimating apparatus while the driver is riding on the vehicle, and the sleepiness and the like of the driver may be estimated by a known method, for example, based on the estimated heart rate of the driver. When setting the heart rate estimating apparatus within the vehicle, the heart rate estimating apparatus may be mounted on a steering wheel, a seat, a door, and the like, for example.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A heart rate estimating apparatus comprising:
   a transmitter configured to transmit microwave with respect to a subject;
   a receiver configured to receive and detect reflected wave from the subject irradiated with the microwave, and acquire a detected result;
   a sensor configured to sense a movement of the subject, and acquire a sensed result;
   a storage unit configured to store a program; and
   a processor configured to execute the program stored in the storage unit and perform a process including
      performing a first frequency analysis of the detected result to obtain a first result of the first frequency analysis versus frequency, wherein the first result includes feature points that are formed by peaks having a first amplitude or greater;
      performing a second frequency analysis of the sensed result to obtain a second result of the second frequency analysis versus frequency, wherein the second result includes feature points that are formed by peaks having a second amplitude or greater; and
      estimating a heart rate based on feature points remaining after excluding the feature points included in the first result and located at frequencies within a predetermined frequency range of frequencies of the peaks forming the feature points included in the second result.

2. The heart rate estimating apparatus as claimed in claim 1, wherein the sensor includes at least one of a microphone, an acceleration sensor, and an angular velocity sensor.

3. The heart rate estimating apparatus as claimed in claim 1, wherein the predetermined frequency range is 0.5 Hz or higher and 4.0 Hz or lower.

4. The heart rate estimating apparatus as claimed in claim 1, wherein the estimating performs a filter process with respect to the detected result, using a frequency of one of the peaks forming the feature points remaining after excluding the feature points included in the first result and located at the frequencies within the predetermined frequency range, as a center of the filter process.

5. The heart rate estimating apparatus as claimed in claim 4, wherein the processor performs the process further including
   performing a first order differentiation on output data of the filter process to acquire a heart beat interval; and
   computing the heart rate based on the heart beat interval.

6. A heart rate estimating method comprising:
   acquiring a detected result from a receiver that receives and detects reflected wave from a subject irradiated with microwave;
   acquiring a sensed result from a sensor that senses a movement of the subject;
   performing, by a processor, a first frequency analysis of the detected result to obtain a first result of the first frequency analysis versus frequency, wherein the first result includes feature points that are formed by peaks having a first amplitude or greater;
   performing, by the processor, a second frequency analysis of the sensed result to obtain a second result of the second frequency analysis versus frequency, wherein the second result includes feature points that are formed by peaks having a second amplitude or greater; and
   estimating, by the processor, a heart rate based on feature points remaining after excluding the feature points included in the first result and located at frequencies within a predetermined frequency range of frequencies of the peaks forming the feature points included in the second result.

7. The heart rate estimating method as claimed in claim 6, wherein the acquiring the sensed result senses the movement by at least one of a microphone, an acceleration sensor, and an angular velocity sensor.

8. The heart rate estimating method as claimed in claim 6, wherein the predetermined frequency range is 0.5 Hz or higher and 4.0 Hz or lower.

9. The heart rate estimating method as claimed in claim 6, wherein the estimating performs a filter process with respect to the detected result, using a frequency of one of the peaks forming the feature points remaining after excluding the feature points included in the first result located at the frequencies within the predetermined frequency range, as a center of the filter process.

10. The heart rate estimating method as claimed in claim 9, further comprising:

performing, by the processor, a first order differentiation on output data of the filter process to acquire a heart beat interval; and computing, by the processor, the heart rate based on the heart beat interval.

11. A non-transitory computer-readable storage medium having stored therein a program for causing a computer to execute a process for estimating a heart rate, the process comprising:

acquiring a detected result that indicates a reflected wave from a subject irradiated with microwave;

acquiring a sensed result that indicates a movement of the subject;

performing a first frequency analysis of the detected result to obtain a first result of the first frequency analysis versus frequency, wherein the first result includes feature points that are formed by peaks having a first amplitude or greater;

performing a second frequency analysis of the sensed result to obtain a second result of the second frequency analysis versus frequency, wherein the second result includes feature points that are formed by peaks having a second amplitude or greater; and estimating a heart rate based on feature points remaining after excluding the feature points included in the first result and located at frequencies within a predetermined frequency range of frequencies of the peaks forming the feature points included in the second result.

12. The non-transitory computer-readable storage medium as claimed in claim 11, wherein the a predetermined frequency range is 0.5 Hz or higher and 4.0 Hz or lower.

13. The non-transitory computer-readable storage medium as claimed in claim 11, wherein the estimating performs a filter process with respect to the detected result, using a frequency of one of the peaks forming the feature points remaining after excluding the feature points included in the first result located at the frequencies within the predetermined frequency range, as a center of the filter process.

14. The non-transitory computer-readable storage medium as claimed in claim 13, wherein the process further comprises:

performing a first order differentiation on output data of the filter process to acquire a heart beat interval; and computing the heart rate based on the heart beat interval.

15. The non-transitory computer-readable storage medium as claimed in claim 11, wherein the program for causing the computer to execute the process for estimating the heart rate further causes the computer to execute a process comprising:

estimating respiratory information based on feature points remaining after excluding the feature points included in the first result and located at frequencies within a frequency range of 0.1 Hz or higher and 0.8 Hz or lower of the peaks forming the feature points included in the second result; and performing a filter process with respect to the detected result, using a frequency of one of the peaks forming the feature points remaining after excluding the feature points included in the first result located at the frequencies within the frequency range of 0.1 Hz or higher and 0.8 Hz or lower, as a center of the filter process.

16. The non-transitory computer-readable storage medium as claimed in claim 15, wherein the process further comprises:

performing a first order differentiation on output data of the filter process to acquire a respiration interval; and computing a respiration rate based on the respiration interval.

* * * * *